(12) United States Patent
Whitten et al.

(10) Patent No.: US 9,527,806 B2
(45) Date of Patent: Dec. 27, 2016

(54) STRUCTURE, SYNTHESIS, AND APPLICATIONS FOR POLY (PHENYLENE) ETHYNYLENES (PPES)

(75) Inventors: David G. Whitten, Albuquerque, NM (US); Kirk S. Schanze, Gainesville, FL (US); Anand Parthasarathy, Gainesville, FL (US); Eunkyung Ji, Albuquerque, NM (US); Motokatsu Ogawa, Sherman Oaks, CA (US); Thomas S. Corbitt, Albuquerque, NM (US); Dimitri Dascier, Albuquerque, NM (US); Ying Wang, Albuquerque, NM (US); Linnea K. Ista, Albuquerque, NM (US); Eric H. Hill, Donostia (ES)

(73) Assignees: STC.UNM, Albuquerque, NM (US); University of Florida Research Foundation, Inc., Gainesville, FL (US)

( * ) Notice: Subject to any disclaimer, the term of this patent is extended or adjusted under 35 U.S.C. 154(b) by 614 days.

(21) Appl. No.: 13/809,572

(22) PCT Filed: Jul. 13, 2011

(86) PCT No.: PCT/US2011/043922
§ 371 (c)(1),
(2), (4) Date: Apr. 3, 2013

(87) PCT Pub. No.: WO2012/009484
PCT Pub. Date: Jan. 19, 2012

(65) Prior Publication Data
US 2013/0210828 A1 Aug. 15, 2013

Related U.S. Application Data

(60) Provisional application No. 61/399,483, filed on Jul. 13, 2010, provisional application No. 61/400,122, filed on Jul. 22, 2010, provisional application No. 61/366,850, filed on Jul. 22, 2010, provisional application No. 61/401,832, filed on Aug. 19, 2010, provisional application No. 61/401,825, filed on Aug. 19, 2010, provisional application No. 61/404,236, filed on Sep. 29, 2010, provisional application No. 61/456,552, filed on Nov. 8, 2010, provisional application No. 61/413,878, filed on Nov. 15, 2010, provisional application No. 61/471,800, filed on Apr. 5, 2011, provisional application No. 61/499,097, filed on Jun. 20, 2011.

(51) Int. Cl.
| | | |
|---|---|---|
| C07C 229/00 | (2006.01) | |
| C07C 309/24 | (2006.01) | |
| C07C 217/14 | (2006.01) | |
| C07C 309/11 | (2006.01) | |
| C07C 217/20 | (2006.01) | |
| C07D 333/16 | (2006.01) | |
| C07D 487/08 | (2006.01) | |
| C08G 61/02 | (2006.01) | |
| C08G 75/00 | (2006.01) | |

(52) U.S. Cl.
CPC .......... *C07C 309/24* (2013.01); *C07C 217/14* (2013.01); *C07C 217/20* (2013.01); *C07C 309/11* (2013.01); *C07D 333/16* (2013.01); *C07D 487/08* (2013.01); *C08G 61/02* (2013.01); *C08G 75/00* (2013.01); *C08G 2261/312* (2013.01); *C08G 2261/3328* (2013.01); *C08G 2261/3422* (2013.01)

(58) Field of Classification Search
CPC .... C07C 217/14; C07C 217/20; C07C 309/11; C07C 309/24; C07D 333/16; C07D 487/08; C08G 61/02; C08G 75/00; C08G 2261/312; C08G 2261/3328; C08G 2261/3422
See application file for complete search history.

(56) References Cited

U.S. PATENT DOCUMENTS

| | | | |
|---|---|---|---|
| 4,251,386 | A | 2/1981 | Saeki et al. |
| 5,489,400 | A | 2/1996 | Liu et al. |
| 6,743,640 | B2 | 6/2004 | Whitten et al. |
| 7,122,383 | B2 | 10/2006 | Jones et al. |
| 8,455,265 | B2 | 6/2013 | Whitten et al. |
| 8,598,053 | B2 | 12/2013 | Whitten et al. |
| 8,618,009 | B2 | 12/2013 | Schanze et al. |
| 8,753,570 | B2 | 6/2014 | Whitten et al. |
| 9,005,540 | B2 | 4/2015 | Schanze et al. |

(Continued)

FOREIGN PATENT DOCUMENTS

| | | |
|---|---|---|
| JP | 3198365 B2 | 11/1994 |
| WO | WO-2008/143731 A2 | 11/2008 |

(Continued)

OTHER PUBLICATIONS

Wosnick et al.( Synthesis and Application of Poly(phenylene Ethynylene)s for Bioconjugation: A Conjugated Polymer-Based Fluorogenic Probe for Proteases American Chemical Society 2005, 127, 3400-3405).*

(Continued)

*Primary Examiner* — Yevegeny Valenrod
*Assistant Examiner* — Blaine G Doletski
(74) *Attorney, Agent, or Firm* — Schwegman Lundberg & Woessner, P.A.

(57) ABSTRACT

The present disclosure provides novel poly(phenylene ethynylene) (PPE) compounds, methods for synthesizing these compounds, and materials and substances incorporating these compounds. The various PPEs show antibacterial, antiviral and antifungal activity.

17 Claims, 22 Drawing Sheets

(56) References Cited

U.S. PATENT DOCUMENTS

| | | | |
|---|---|---|---|
| 2002/0177828 A1* | 11/2002 | Batich | A01N 25/34 604/367 |
| 2003/0134959 A1 | 7/2003 | Hancock et al. | |
| 2003/0168756 A1 | 9/2003 | Balkus, Jr. et al. | |
| 2003/0178607 A1 | 9/2003 | Swager et al. | |
| 2004/0241768 A1 | 12/2004 | Whitten et al. | |
| 2005/0059168 A1 | 3/2005 | Bazan et al. | |
| 2005/0148254 A1* | 7/2005 | Lu | A01N 33/12 442/123 |
| 2006/0120923 A1 | 6/2006 | Swager et al. | |
| 2006/0175193 A1 | 8/2006 | Inganas et al. | |
| 2007/0215841 A1 | 9/2007 | Ford et al. | |
| 2008/0090021 A1 | 4/2008 | Long et al. | |
| 2011/0159605 A1 | 6/2011 | Whitten et al. | |
| 2011/0223058 A1 | 9/2011 | Whitten et al. | |
| 2011/0293470 A1 | 12/2011 | Schanze et al. | |
| 2012/0271023 A1 | 10/2012 | Whitten et al. | |
| 2013/0273800 A1 | 10/2013 | Whitten et al. | |
| 2014/0086795 A1 | 3/2014 | Schanze et al. | |

FOREIGN PATENT DOCUMENTS

| | | |
|---|---|---|
| WO | WO-2009/158606 A9 | 12/2009 |
| WO | WO-2009158606 A2 | 12/2009 |
| WO | WO-2010/054304 A2 | 5/2010 |
| WO | WO-2011/044580 A3 | 4/2011 |
| WO | WO-2012/009472 A2 | 1/2012 |
| WO | WO-2012009484 A2 | 1/2012 |

OTHER PUBLICATIONS

Ding et al. (Insight into the Mechanism of Antimicrobial Poly(phenylene ethynylene) Polyelectrolytes: Interactions with Phosphatidylglycerol Lipid Membranes, American Chemical Society, Langmuir, 25(24), 13742-13751, 2009).*

Kim et al. (Complexation of Anionic Conjugated Polyelectrolyte with Cationic Surfactant Macromolecular Research, vol. 13, No. 5, pp. 460-462 2005).*

Tan et al. (Hyper-Efficient Quenching of a Conjugated Polyelectrolyte by Dye-Doped Silica Nanoparticles: Better Quenching in the Nonaggregated State, Langmuir Letter, 26(3), 1528-1532, Nov. 19, 2009).*

Corbit et al. (Conjugated Polyelectrolyte Capsules: Light-Activated Antimicrobial Micro "Roach Motels" Applied Materials and Interfaces, vol. 1 No. 1, 48-52, Nov. 24, 2008).*

"International Application Serial No. PCT/US2011/043922, International Prelimary Report on Patentability mailed Jan. 15, 2013", 4 pgs.

Bartlett, Grant R., "Phosphorus Assay in Column Chromatography", *The Journal of Biological Chemistry*, 234(3), (1959), 466-468.

Ding, Liping, et al., "Insight into the Mechanism of Antimicrobial Poly(phenylene ethynylene) Polyelectrolytes: Interactions with Phosphatidylglycerol Lipid Membranes", *Langmuir*, 25(24), (2009), 13742-13751.

Galaev, I. Y., "'Smart' polymers in biotechnology and medicine", *Russian Chemical Reviews*, 64(5), (1995), 471-489.

Hoffman, Allan S., "Bioconjugates of Intelligent Polymers and Recognition Proteins for Use in Diagnostics and Affinity Separations", *Clinical Chemistry*, 46:9, (2000), 1478-1486.

Schild, H. G., "Poly(N-Isopropylacrylamide): Experiment, Theory and Application", *Prog. Polym. Sci.*, 17, (1992), 163-249.

International Application Serial No. PCT/US2011/043922, International Search Report mailed Mar. 19, 2012, 3 pgs.

International Application Serial No. PCT/US2011/043922, Written Opinion mailed Mar. 19, 2012, 3 pgs.

Kim, Chae Kyu, et al., "Complexation of Anionic Conjugated Polyelectrolyte with Cationic Surfactant", Macromolecular Research, vol. 13 No. 5, (Oct. 31, 2005), 460-462.

Wang, Ying, et al., "Membrane Perturbation Activity of Cationic Phenylene Ethynylene and Polymers: Selectivity against Model Bacterial and Mammalian Membranes", Langmuir, 26(15), (Jun. 29, 2010), 12509-12514.

"U.S. Appl. No. 12/529,390, Examiner Interview Summary mailed Jan. 31, 2012", 3 pgs.

"U.S. Appl. No. 12/529,390, Examiner Interview Summary mailed Nov. 13, 2012", 3 pgs.

"U.S. Appl. No. 12/529,390, Non Final Office Action mailed Jul. 18, 2012", 7 pgs.

"U.S. Appl. No. 12/529,390, Non-Final Office Action mailed Nov. 1, 2011", 11 pgs.

"U.S. Appl. No. 12/529,390, Notice of Allowance mailed Feb. 5, 2013", 10 pgs.

"U.S. Appl. No. 12/529,390, Preliminary Amendment mailed Sep. 1, 2009", 13 pgs.

"U.S. Appl. No. 12/529,390, Response filed May 1, 2012 to Non Final Office Action mailed Nov. 1, 2011", 19 pgs.

"U.S. Appl. No. 12/529,390, Response filed Dec. 18, 2012 to Non Final Office Action mailed Jul. 18, 2012", 16 pgs.

"U.S. Appl. No. 13/001,478 , Response filed Dec. 19, 2013 to Non Final Office Action mailed Oct. 3, 2013", 10 pgs.

"U.S. Appl. No. 13/001,478, Non Final Office Action mailed Oct. 3, 2013", 6 pgs.

"U.S. Appl. No. 13/001,478, Notice of Allowance mailed Jan. 31, 2014", 7 pgs.

"U.S. Appl. No. 13/001,478, Response filed Jul. 11, 2013 to Restriction Require mailed Jun. 13, 2013", 9 pgs.

"U.S. Appl. No. 13/001,478, Restriction Requirement mailed Jun. 13, 2013", 7 pgs.

"U.S. Appl. No. 13/128,571, Response filed May 13, 2013 to Non Final Office Action mailed Feb. 13, 2013", 12 pgs.

"U.S. Appl. No. 13/128,571, Response filed Nov. 19, 2012 to Restriction Requirement mailed Oct. 17, 2012", 6 pgs.

"U.S. Appl. No. 13/128,571, Non Final Office Action mailed Feb. 13, 2013", 10 pgs.

"U.S. Appl. No. 13/128,571, Notice of Allowance mailed Aug. 28, 2013", 9 pgs.

"U.S. Appl. No. 13/128,571, Preliminary Amendment filed May 10, 2011", 5 pgs.

"U.S. Appl. No. 13/128,571, Restriction Requirement mailed Oct. 17, 2012", 6 pgs.

"U.S. Appl. No. 13/503,067 , Response filed Mar. 11, 2013 to Non Final Office Action mailed Oct. 10, 2012", 11 pgs.

"U.S. Appl. No. 13/503,067 , Response filed Jul. 11, 2013 to Final Office Action mailed Jun. 6, 2013", 7 pgs.

"U.S. Appl. No. 13/503,067, Final Office Action mailed Jun. 6, 2013", 11 pgs.

"U.S. Appl. No. 13/503,067, Non Final Office Action mailed Oct. 10, 2012", 11 pgs.

"U.S. Appl. No. 13/503,067, Notice of Allowance mailed Aug. 2, 2013", 10 pgs.

"U.S. Appl. No. 13/809,573, Response filed Sep. 24, 2015 to Restriction Requirement mailed Jul. 24, 2015", 9 pgs.

"U.S. Appl. No. 13/809,573, Restriction Requirement mailed Jul. 24, 2015", 7 pgs.

"U.S. Appl. No. 14/092,409, Notice of Allowance mailed Dec. 10, 2014", 10 pgs.

"European Serial No. 09771137.8, Office Action mailed Feb. 9, 2011", 1 pg.

"European Application Serial No. 09771137.8, Office Action mailed Feb. 14, 2011", 2 pgs.

"European Application Serial No. 09771137.8, Office Action mailed Mar. 3, 2011", 1 pg.

"European Application Serial No. 09771137.8, Office Action mailed Mar. 16, 2011", 1 pg.

"European Application Serial No. 09771137.8, Response filed Feb. 18, 2011 to Office Action mailed Feb. 9, 2011", 6 pgs.

"International Application Serial No. PCT/US2008/002756, International Preliminary Report on Patentability mailed Sep. 1, 2009", 6 pgs.

"International Application Serial No. PCT/US2008/002756, International Search Report mailed Feb. 25, 2009", 2 pgs.

(56) References Cited

OTHER PUBLICATIONS

"International Application Serial No. PCT/US2008/002756, Written Opinion mailed Feb. 25, 2009", 5 pgs.
"International Application Serial No. PCT/US2009/048838, International Preliminary Report on Patentability mailed Jan. 5, 2011", 7 pgs.
"International Application Serial No. PCT/US2009/048838, International Search Report mailed Apr. 30, 2010", 4 pgs.
"International Application Serial No. PCT/US2009/048838, Witten Opinion mailed Apr. 30, 2010", 6 pgs.
"International Application Serial No. PCT/US2009/063715, International Preliminary Report on Patentability mailed May 10, 2011", 6 pgs.
"International Application Serial No. PCT/US2009/063715, International Search Report mailed May 27, 2010", 4 pgs.
"International Application Serial No. PCT/US2009/063715, Written Opinion mailed May 27, 2010", 5 pgs.
"International Application Serial No. PCT/US2010/052332, International Preliminary Report on Patentability mailed Apr. 11, 2012", 7 pgs.
"International Application Serial No. PCT/US2010/052332, International Search Report mailed Jun. 24, 2011", 4 pgs.
"International Application Serial No. PCT/US2010/052332, Written Opinion mailed Jun. 24, 2011", 6 pgs.
"International Application Serial No. PCT/US2011/043908, International Preliminary Report on Patentability mailed Jan. 15, 2013", 7 pgs.
"International Application Serial No. PCT/US2011/043908, International Search Report and Written Opinion mailed Apr. 6, 2012", 11 pgs.
Arnt, Lachelle, et al., "New Poly(phenyleneethynylene)s with Cationic, Facially Amphiphilic Structures", Journal of the American Chemical Society,124(26), (2002), 7664-7665.
Bruns, R., et al., "Chapter 3—R&D in material protection: New biocides", In: Directory of Microbicides for the Protection of Materials—A Handbook, Paulus, W., Editor, (2005), 25-46.
Shemburu, Sireesha, et al., "Light-Induced Biocidal Action of Conjugated Polyelectrolytes Supported on Colloids", Langmuir, 24, (2008), 11053-11062.
Choi, W. S., et al., "Synthesis of Two Types of Nanoparticles in Polyelectrolyte Capsule Nanoreactors and Their Dual Functionality", J. Am. Chem. Soc., 127, (2005), 16136-16142.
Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.
Corbitt, Thomas S., et al., "Conjugated Polyelectrolyte Capsules: Light-Activated Antimicrobial Micro "Roach Motels"†", ACS Appl. Mater. Interfaces, 1(1), (2009), 48-52.
De Geest, B. G., et al., "Release mechanisms for polyelectrolyte capsules", Chem. Soc. Rev., 36, (2007), 636-649.
Ean, Qu-Li, et al., "Water-Soluble Cationic Poly(p-phenyleneethynylene)s (PPEs): Effects of Acidity and Ionic Strength on Optical Behavior.", Macromolecules.vol. 38, (2005), 2927-2936.
George, Wayne N., et al., "Amplified fluorescence quenching in high ionic strength media.", Soft Matter. vol. 3, (2007), 1381-1387.
Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.
Lin, Ching-Yao, et al., "Design and Characterization of Novel Porphyrins with Oligo(phenylethylnyl) Links of Varied Length for Dye-Sensitized Solar Cells: Synthesis and Opitical, Electrochemical, and Photovoltaic Investigation", J. Phys. Chem. C., 113(2), (2009), 755-764.
Lu, L., et al., "Biocidal Activity of a Light-Absorbing Fluorescent Conjugated Polyelectrolyte", Langmuir, 21, (2005), 10154-10159.
Ogawa, Katsu, et al., "Conjugated Polyelectrolyte-Grafted Silica Microspheres", Langmuir, 23(8), (2007), 4541-4548.
Tan, C, et al., "Photophysics, aggregation and amplified quenching of a water-soluble poly (phenylene ethynylene)", Chem. Commun., (2002), 446-447.
Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.
Tang, Yanli, et al., "Synthesis, Self-Assembly, and Photophysical Behavior of Oligo Phenylene Ethynylenes: From Molecular to Supramolecular Properties", Langmuir, 25(1), (2009), 21-25.
Tew, G. N, et al., "", Biochimica et Biophysica Acta 2006, (2006), 1387-1392.
Tiller, J. C., et al., "Designing surfaces that kill bacteria on contact", Proc. Natl. Acad. Sci. USA, 98(11), (May 22, 2001), 5981-5985.
Tong, W., et al., "Single Polyelectrolyte Microcapsules Fabricated by Glutaraldehyde-Mediated Covalent Layer-By-Layer Assembly", Macromol. Rapid Commun., 27, (2006), 2078-2083.
Wang, Z., et al., "Preparation and application of single polyelectrolyte microcapsules possessing tunable autofluorescent properties.", Colloids and Surfaces A: Physicochemical and Engineering Aspects, 329, (2008), 58-66.
Yang, Chaoyong James, et al., "Direct Synthesis of an Oligonucleofide-Poly-(phenylene ethynylene) Conjugate with a Precise One-to-One Molecular Ratio", Angew. Chem. Int. Ed. 44, (2005), 2572-2576.
Zhu, Huiguang, et al., "Synthesis of Size-Controlled Monodisperse Manganese Carbonate Microparticles as Templates for Uniform Polyelectrolyte Microcapsule Formation.", Chem. Mater.,17, (2005), 2323-2328.
"U.S. Appl. No. 13/809,573, Non Final Office Action mailed Jan. 22, 2016", 13 pgs.
"U.S. Appl. No. 13/809,573, Preliminary Amendment filed Jan. 10, 2013", 9 pgs.
Wang, Ying, et al., "Membrane Perturbation Activity of Cationic Phenylene Ethynyiene Oligomers and Polymers", Langmuir Letter, 26(15), (2010), 12509-12514.
Zhinjou, Zhou, "Studies of a cyanine-based biosensor and light-induced antibacterial activities of oligophenyleneethynylenes", Dissertation, Chemistry, University of New Mexico, Albuquerque, NM, (Dec. 2010), 165 pages.

* cited by examiner n=7, 9, 11, 14, 20 and 49 n=5, 9, 12, and 23 n=11, and 40

STRUCTURE, SYNTHESIS, AND APPLICATIONS FOR POLY (PHENYLENE) ETHYNYLENES (PPES)

STATEMENT REGARDING GOVERNMENT SPONSORED RESEARCH

This invention was made with Government support under grant number W911NF-07-0079 awarded by the Defense Threat Reduction Agency. The U.S. Government has certain rights in this invention.

CROSS-REFERENCE TO RELATED APPLICATIONS

This application is a U.S. National Stage Application under 35 U.S.C. 371 from International Application No. PCT/US2011/043922, filed Jul. 13, 2011 which claims benefit of U.S. Provisional Application Nos. 61/399,483, filed Jul. 13, 2010; 61/400,122, filed Jul. 22, 2010; 61/366,850, filed Jul. 22, 2010; 61/401,825, filed Aug. 19, 2010; 61/401,832, filed Aug. 19, 2010; 61/404,236, filed Sep. 29, 2010; 61/456,552, filed Nov. 8, 2010; 61/413,878, filed Nov. 15, 2010; 61/471,800 filed Apr. 5, 2011; and 61/499,097 filed Jun. 20, 2011; each of which is hereby incorporated by reference in its entirety.

BACKGROUND

Poly(phenylene ethynylene) based conjugated polyelectrolytes (also referred to herein as Poly(phenylene ethynylenes) or (PPEs)) are conjugated molecules that have a wide range of applications in electrically conducting materials, bio-chemical sensors, and supramolecular assemblies. More recently, interest has developed in the antimicrobial activity of these compounds. For example, while the extensive use of antibiotics has successfully dramatically reduced the human mortality rate due to infections, it has also given rise to the acquisition of resistance genes by various organisms, making some infections increasingly hard to treat. Accordingly novel methods for infection control, including novel methods and compounds for providing antimicrobial properties to a variety of materials is greatly desired.

SUMMARY

The present disclosure provides novel poly(phenylene ethynylene) (PPE) compounds, methods for synthesizing these compounds, and materials incorporating these compounds.

According to an embodiment, the PPEs of the present disclosure have the base structure shown in FIG. 1 where:

n is selected from the group consisting of the whole numbers between 5 and 200;

A is selected from the group consisting of $C_2C_6H_2$ and $C_2C_4H_2S$;

$B=C_2C_6H_2$,

C=is either $C_6H_4$ or not present;

X is selected from the group consisting of: H, $[C_2C_6H_4]_2COOCH_2CH_3$, and; $[C_2C_4H_2S][C_2C_6H_4]COOCH_2CH_3$, Y is selected from the group consisting of: H and $COOCH_2CH_3$, $Z_A$ is selected from the group consisting of $O(CH_2)_k(C_6H_{12}N_2)C_6H_{13}^{2+}$, $O(CH_2)_kSO_3^-$, $O(CH_2)_kN(CH_2CH_3)_3^+$, and $O(CH_2)_kN(CH_3)_3^+$; where k is selected from the group consisting of the whole number between 1 and 10;

$Z_B$ is selected from the group consisting of H and $(OCH_2CH_2)_3OCH_3$, wherein:

if $Z_A$ as $O(CH_2)_k(C_6H_{12}N_2)C_6H_{13}^{2+}$, then $Z_B$ is H, $A=C_2C_6H_2$, if present, is $C_6H_4$, and X is selected from the group consisting of H and $[C_2C_6H_4]_2COOCH_2CH_3$, wherein:

if X is H, then Y is H; and C is not present if X is $[C_2C_6H_4]_2COOCH_2CH_3$, then Y is $COOCH_2CH_3$ and C is $C_6H_4$;

if $Z_A$ is $O(CH_2)_kSO_3^-$, $Z_B$ is H, $A=C_2C_6H_2$, C is not present, and X=Y=H;

if $Z_A$ is $O(CH_2)_kN(CH_2CH_3)_3^+$, then $Z_B$ is $(OCH_2CH_2)_3OCH_3$, $A=C_2C_6H_2$, C is not present, and X=Y=H;

if $Z_A$ is $O(CH_2)_kN(CH_3)_3^+$, and $Z_B$ is $(OCH_2CH_2)_3OCH_3$, then C is not present, $A=C_2C_4H_2$ and X=Y=H;

if $Z_A$ is $O(CH_2)_kN(CH_3)_3^+$, $Z_B$ is H, and C is not present, then $A=C_2C_4H_2S$ and X=Y=H;

if $Z_A$ is $O(CH_2)_kN(CH_3)_3^+$, $Z_B$ is H, and C is present, then $Y=COOCH_2CH_3$ and X is selected from the group consisting of $[C_2C_6H_4]_2COOCH_2CH_3$ and $[C_2C_4H_2S][C_2C_6H_4]COOCH_2CH_3$; wherein if $A=C_2C_6H_2$, then X is $[C_2C_6H_4]_2COOCH_2CH_3$;

if $A=C_2C_6H_2S$, then X is $[C_2C_4H_2S][C_2C_6H_4]COOCH_2CH_3$.

DETAILED DESCRIPTION

The present disclosure provides a plurality of novel compounds generally referred to herein as poly (phenylene ethynylenes) (PPEs), methods of synthesizing PPEs and various uses for the PPEs. According to an embodiment, the present disclosure provides PPEs having the general structure shown in FIG. 1, where:

n is selected from the group consisting of the whole numbers between 5 and 200;

A is selected from the group consisting of $C_2C_6H_2$ and $C_2C_4H_2S$;

$B = C_2C_6H_2$;

C= is either $C_6H_4$ or not present;

X is selected from the group consisting of: H, $[C_2C_6H_4]_2COOCH_2CH_3$, and; $[C_2C_4H_2S][C_2C_6H_4]COOCH_2CH_3$, Y is selected from the group consisting of: H and $COOCH_2CH_3$, $Z_A$ is selected from the group consisting of $O(CH_2)_k(C_6H_{12}N_2)C_6H_{13}^{2+}$, $O(CH_2)_kSO_3^-$, $O(CH_3)_kN(CH_2CH_3)_3^+$, and $O(CH_2)_kN(CH_3)_3^+$; where k is selected from the group consisting of the whole number between 1 and 10;

$Z_B$ is selected from the group consisting of H and $(OCH_2CH_2)_3OCH_3$, wherein:

if $Z_A$ is $O(CH_2)_k(C_6H_{12}N_2)C_6H_{13}^{2+}$, then $Z_B$ is H, $A=C_2C_6H_2$, C, if present, is $C_6H_4$, and X is selected from the group consisting of H and $[C_2C_6H_4]_2COOCH_2CH_3$, wherein:

if X is H, then Y is H; and C is not present if X is $[C_2C_6H_4]_2COOCH_2CH_3$, then Y is $COOCH_2CH_3$ and C is $C_6H_4$;

if $Z_A$ is $O(CH_2)_kSO_3^-$, $Z_B$ is H, $A=C_2C_6H_2$, C is not present, and X=Y=H;

if $Z_A$ is $O(CH_2)_kN(CH_2CH_3)_3^+$, then $Z_B$ is $(OCH_2CH_2)_3OCH_3$, $A=C_2C_6H_2$, C is not present, and X=Y=H;

if $Z_A$ is $O(CH_2)_kN(CH_3)_3^+$, and $Z_B$ is $(OCH_2CH_2)_3OCH_3$, then C is not present, $A=C_2C_4H_2$ and X=Y=H;

if $Z_A$ is $O(CH_2)_kN(CH_3)_3^+$, $Z_B$ is H, and C is not present, then $A=C_2C_4H_2S$ and X=Y=H;

if $Z_A$ is $O(CH_2)_kN(CH_3)_3^+$, $Z_B$ is H, and C is present, then $Y=COOCH_2CH_3$ and X is selected from the group consisting of $[C_2C_6H_4]_2COOCH_2CH_3$ and $[C_2C_4H_2S][C_2C_6H_4]COOCH_2CH_3$; wherein if $A=C_2C_6H_2$, then X is $[C_2C_6H_4]_2COOCH_2CH_3$;

if $A=C_2C_6H_2S$, then X is $[C_2C_4H_2S][C_2C_6H_4]COOCH_2CH_3$.

The PPEs disclosed herein can exist in solution, in colloidal suspensions, and attached, for example, by modification of the carboxyester "headgroup," to surfaces by various covalent linkages. All of the PPEs disclosed herein are fluorescent and demonstrate biocidal activity. Furthermore, some of the compounds have demonstrated viricidal and/or fungicidal activity as well.

Figure 1:
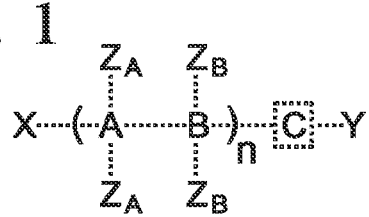
FIG. 1 depicts the basic structure of PPE according to an embodiment of the present disclosure.
Figure 2:
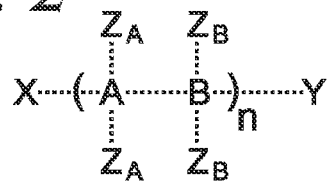
FIG. 2 depicts the basic structure of a PPE according to another embodiment of the present disclosure.

In general, the PPEs disclosed herein are formed from a single oxygen generator resonant structure core unit shown in FIG. 2 as (A and B) and a plurality of functional groups extending from the core unit. More specifically, the PPEs disclosed herein contain para-linked subunits of a conjugated aromatic oligomeric chain (A and B) with attached functional groups X and Y at the termini of the chain and functional groups $Z_A$, attached to the aromatic ring of subunit A and $Z_B$ attached to the aromatic ring of subunit B. Some of the PPEs disclosed herein may include a third resonant structure C, as shown in FIG. 1, which is an optional aromatic linking unit for functional group Y.

According to various embodiments, the specific PPEs of the present disclosure obtained by various substitutes of the general structure shown in FIG. 1. Table 1 provides a list of the various substitutions that give rise to the PPEs of the present disclosure.

TABLE 1

FIG. 1 Substitutions

| A | B | C | X = | Y = | $Z_A$ = | $Z_B$ = | n = | k = |
|---|---|---|---|---|---|---|---|---|
| $C_2C_6H_2$ | $C_2C_6H_2$ | none | H | H | $O(CH_2)_k(C_6H_{12}N_2)C_6H_{13}^{2+}$ | H | 5-200 | 1-10 |
| $C_2C_6H_2$ | $C_2C_6H_2$ | none | H | H | $O(CH_2)_kSO_3^-$ | H | 5-200 | 1-10 |
| $C_2C_6H_2$ | $C_2C_6H_2$ | none | H | H | $O(CH_2)_kN(CH_2CH_3)_3^+$ | $(OCH_2CH_2)_3OCH_3$ | 5-200 | 1-10 |
| $C_2C_6H_2$ | $C_2C_6H_2$ | none | H | H | $O(CH_2)_kN(CH_3)_3^+$ | $(OCH_2CH_2)_3OCH_3$ | 5-200 | 1-10 |
| $C_2C_6H_2$ | $C_2C_6H_2$ | none | H | H | $O(CH_2)_kN(CH_3)_3^+$ | $(OCH_2CH_2)_3OCH_3$ | 5-200 | 1-10 |
| $C_2C_6H_2$ | $C_2C_6H_2$ | $C_6H_4$ | $[C_2C_6H_4]_2COOCH_2CH_3$ | $COOCH_2CH_3$ | $O(CH_2)_kN(CH_3)_3^+$ | H | 5-200 | 1-10 |
| $C_2C_6H_2$ | $C_2C_6H_2$ | $C_6H_4$ | $[C_2C_6H_4]_2COOCH_2CH_3$ | $COOCH_2CH_3$ | $O(CH_2)_k(C_6H_{12}N_2)C_6H_{13}^{2+}$ | H | 5-200 | 1-10 |
| $C_2C_4H_2S$ | $C_2C_6H_2$ | $C_6H_4$ | $[C_2C_4H_2S][C_2C_6H_4]COOCH_2CH_3$ | $COOCH_2CH_3$ | $O(CH_2)_kN(CH_3)_3^+$ | H | 5-200 | 1-10 |

In viewing the chart above, those of skill in the art recognize that compounds can easily be formed to include various numbers of repeat units alkyl chain linkages to the quaternary ammonium bearing groups and/or the sulfonate bearing groups, as demonstrated, for example, by the k groups indicated above. Accordingly, while specific structures and methods of synthesis are disclosed below, it will be understood that similar structures bearing these repeat units are similarly contemplated by the present disclosure.

Figure 3:
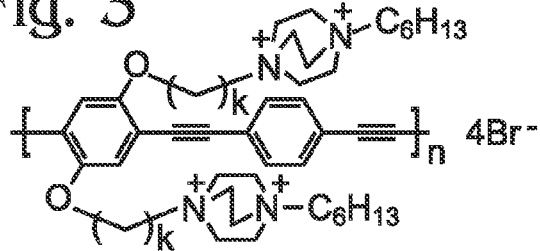
FIG. 3 is the chemical structure of PPE-DABCO.
Figure 11:
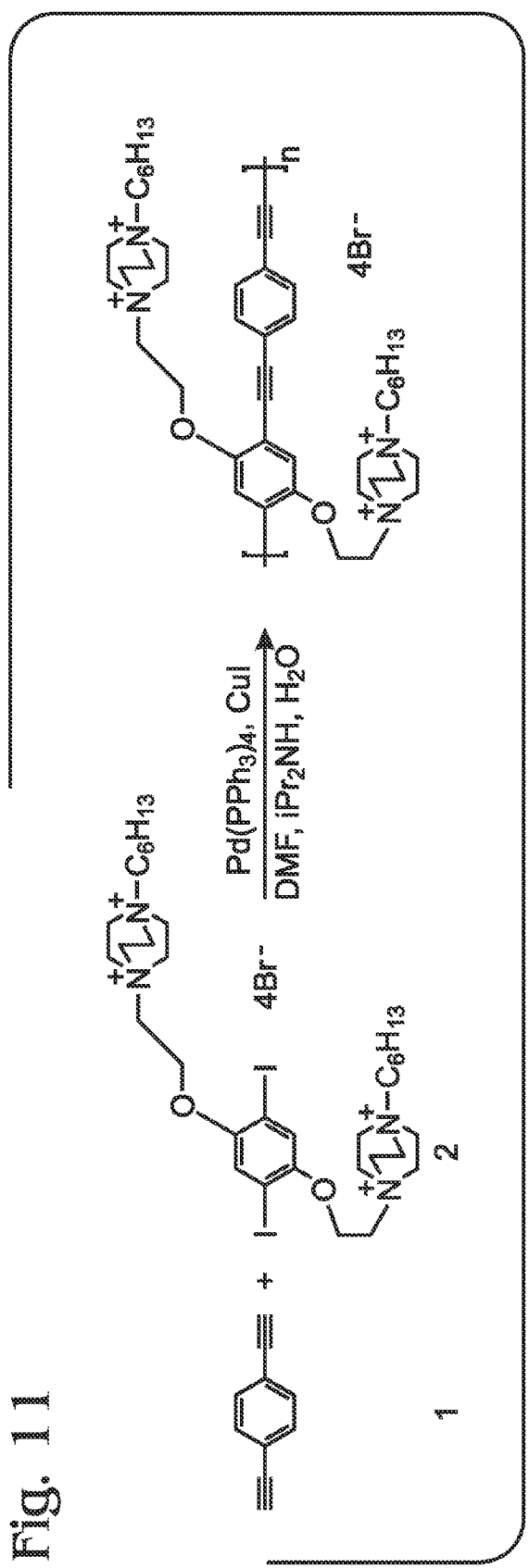
FIG. 11 is a schematic illustration of the synthesis scheme for PPE-DABCO.

FIG. 3 shows the chemical structure of PPE-DABCO. Suitable counter ions for PPE-DABCO include Cl−, Br− or I−. An exemplary synthesis scheme for PPE-DABCO where k=3 is shown in FIG. 11. Synthesis for the scheme shown in FIG. 11 is as described below:

1,4-diethynylbenzene was synthesized and purified as described in Takahashi, S.; Kuroyama, Y.; Sonogashira, K.; Hagihara, N. Synthesis (Stuttgart) 1980, 627-630.

1-Hexyl-4-aza-1-azoniabicyclo[2.2.2]octane Bromide (compound 2). Diazabicyclo[2.2.2]octane (10.0 g, 89.2 mmol) and hexyl bromide (6.3 mL, 44.6 mmol) were combined in 100 mL of ethyl acetate. The solution was stirred for 24 h, after which time, a white precipitate had formed. The solid was collected by vacuum filtration, rinsed with ethyl acetate, and dried under vacuum, yield 11.23 g (91%). 1H NMR (DMSO-d6; H ppm): 0.87 (t, 3 H), 1.28 (m, 6 H), 1.64 (m, 2 H), 3.01 (t, 6 H), 3.22 (m, 2 H), 3.32 (t, 6 H).

4,4′-(2,2′-(2,5-Diiodo-1,4-phenylene)bis(oxy)bis(ethane-2,1-diyl)bis(1-hexyl-1,4-diazonia-bicyclo[2.2.2]octane) Tetrabromide. A solution of 5.8 g (10 mmol) of 1,4-diiodo-2,5-bis(2-bromoethoxy)benzene and 7.0 g (25 mmol) of 5 in 100 mL of dimethylacetamide was stirred at 110° C. for 6 h. Upon cooling, 200 mL of cold ether was added to the reaction mixture. The resulting white precipitate was collected by filtration and recrystallized twice from water, yield 9.8 g (86%). 1H NMR (DMSO-d6; σ ppm): 0.87 (t, 6 H), 1.32 (m, 12 H), 1.72 (m, 4 H), 3.59 (m, 4 H), 3.98 (t, 12 H), 4.14 (m, 16 H), 4.55 (m, 4 H), 7.57 (s, 1 H). 13C NMR (DMSO-d6; σ ppm): 13.83, 21.25, 21.80, 25.17, 30.59, 50.27, 51.38, 62.59, 63.12, 63.33, 87.16, 123.09, 152.11. Elemental analysis calcd for C34H60Br4I2N4O2: C, 36.13; H, 5.35; N, 4.96. Found: C, 35.19; H, 5.60; N, 4.61.

Polymerization Reactions. All of the polymers were prepared from the corresponding monomers to a similar procedure.

Figure 4:
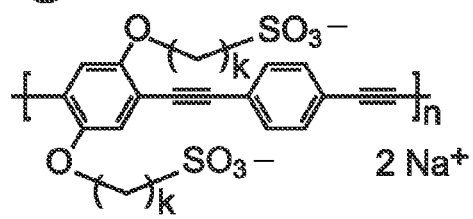
FIG. 4 is the chemical structure of PPE-SO3.
Figure 12:
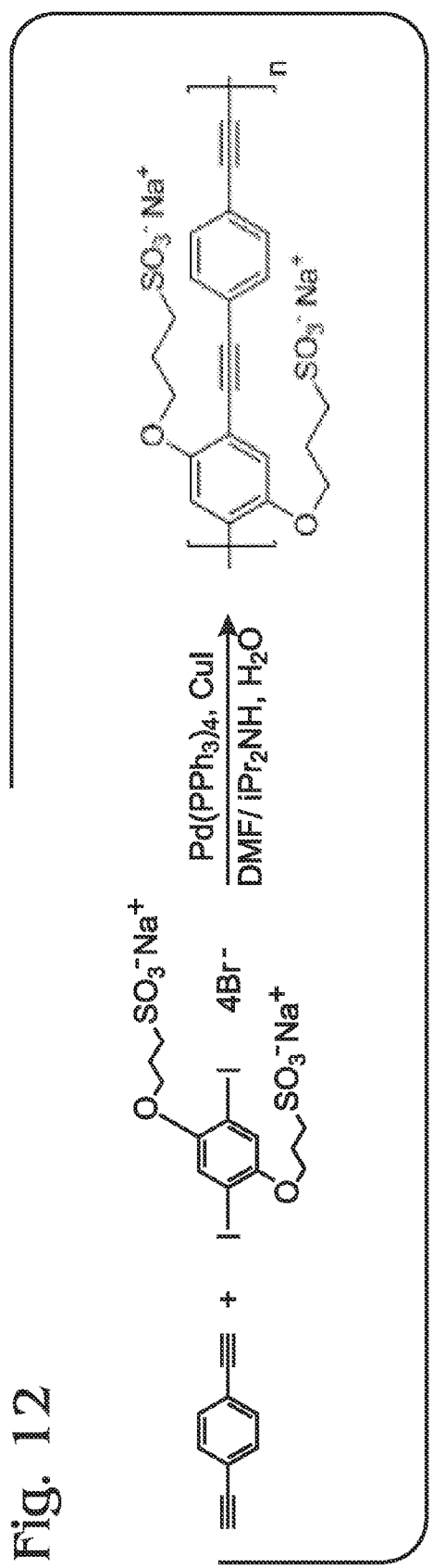
FIG. 12 is a schematic illustration of the synthesis scheme for PPE-SO3.

FIG. 4 shows the chemical structure of PPE-SO3. Suitable counter ions for PPE-DABCO include Na+. An exemplary synthesis scheme for PPE-SO3 where k=3 is shown in FIG. 12. Synthesis for the scheme shown in FIG. 12 is as described below:

Starting Materials 2,5-Diiodohydroquinone and 1,4-diethynylbenzene were synthesized according to procedures published in "Fluorescent Chemosensors Based on Energy Migration in Conjugated Polymers: The Molecular Wire Approach to Increased Sensitivty", Zhou, Q.; Swager, T. M.; J. Am. Chem. Soc. 1995, 117, 12593-12602 and "A convenient synthesis of ethynylarenes and diethynylarenes", Takahashi, S.; Kuroyama, Y.; Sonogashira, K.; Hagihara, N.; Synthesis 1980, 627-630, respectively.

Monomer 1 7.24 g (20.0 mmol) of 2,5-diiodohydroquinone was dissolved in a solution that contained 2.0 g (50.0 mmol) of sodium hydroxide in 200 mL of water in a Erlenmeyer flask under argon. A solution of 6.1 g (50.0 mmol) of 1,3-propanesultone in 40 mL of dioxane was added to the former solution at once. The resulting mixture was then stirred at room temperature overnight, during which time a thick pink slurry formed. The reaction mixture was then stirred at 80-100° C. for another 30 minutes and then cooled in a water/ice bath. The suspension obtained was vacuum filtered, and the retained solid was washed with cold water followed by acetone, and crystallized twice from water.

Yield 9.2 g (70%) as a fine white powder $C_{12}H_{14}I_2Na_2O_8S_2$ (Mol. Wt.; 650.16): Analysis calc: C, 22.17; H, 2.17; I, 39.04; S, 9.86. Analysis found: C, 22.43; H, 2.57; I, 34.63; S, 8.96. FTIR ($v_{max.}$ cm-1, KBr pellet): 2975, 2940, 2872, 1624, 1489, 1464, 1438, 1390, 1353, 1262, 1206, 1156, 1061, 1032, 937, 850, 795, 739, 629, 551 $^1$H-NMR (DMSO-d6; ppm from TMS): 2.00 (t, 4H); 2.64 (t, 4H); 4.05 (t, 4H); 7.30 (s, 2H) $^{13}$C-NMR (DMSO-d6; ppm from TMS): 25.37, 48.14, 68.96, 86.99, 122.44, 152.30

PPE-SO$_3$. 1.008 g (1.55 mmol) of monomer 1 and 0.189 g (1.50 mmol) of 1,4-diethynylbenzene were dissolved in a mixture of 20 mL of water and 20 mL of DMF at 60° C. in a Schlenk flask with a gentle flow of argon and with magnetic stirring. The resulting clear solution was deoxygenated by several cycles of vacuum-argon cycling. Another solution comprised of 52.0 mg (45.0 µmol) of Pd(PPh$_3$)$_4$ and 10.0 mg (45 µmol) of CuI in a mixture of 10 mL of diisopropylamine and 10 mL of DMF was likewise deoxygenated and was subsequently added to the former solution by means of a cannula. The final mixture was again deoxygenated by vacuum-argon cycling and was then warmed to 50-55° C. and stirred under a positive pressure of argon for 14 hrs. The resulting solution was viscous, brown in color and exhibited an intense blue fluorescence when illuminated with a near-UV lamp. The solution was cooled and then slowly added to 1 L of a methanol/acetone/ether mixture (10:40:50 v:v:v). The polymer precipitated as greenish fibers. It was redissolved in 200 mL of water/methanol 70:30, treated with 0.1 g of sodium sulfide ($Na_2S$), and then the solution was filtered through quantitative filter paper, followed by a 10-20 μm fritted glass filter, and finally through a 0.8 μm nylon membrane. The polymer was precipitated by addition to a large volume of methanol/acetone/ether (10:40:50). The polymer was dissolved in water/methanol and reprecipitated from methanol/acetone/ether four more times. Finally, the polymer was dissolved in 150 mL of water, 0.05 g of sodium cyanide was added, and the resulting solution was dialyzed against water (Millipore Nanopure™) using a 6-8 kD MWCO cellulose membrane. After the dialysis, the polymer concentration was approximately 2.1 mg-mL. The polymer was stored in this format and diluted as appropriate for spectroscopic studies. The molecular weight of PPE-$SO_3^-$ was estimated to be 100 kD based on its ultrafiltration properties and iodine end-group analysis.

Yield 535 mg (68.5%) as light yellow fibers $C_{22}H_{18}Na_2O_8S_2$ (Mol. Wt. monomeric unit: 520.48): Analysis calc: C, 50.77; H, 3.49; S, 12.32 Analysis found; C, 48.98; H, 4.52; I, 0.12; S, 8.89 FTIR ($v_{max}$, cm-1, cast film): 2944, 2878, 1638, 1519, 1469, 1439, 1417, 1281, 1189, 1045, 835, 612, 541 $^1$H-NMR (DMSO-d6; δ ppm from TMS, 100° C.): 2.15 (t, 4H); 2.77 (t, 4H); 4.21 (t, 4H); 7.18 (s, 2H); 7.61 (broad, 4H)

Figure 5:
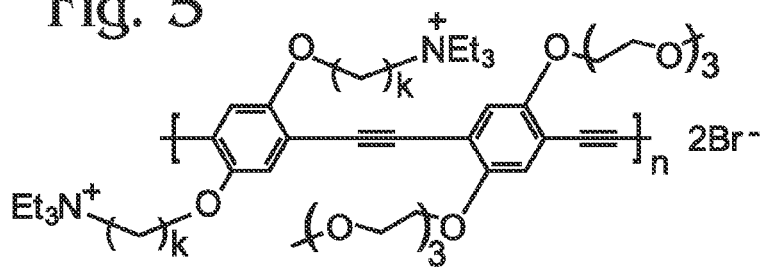
FIG. 5 is the chemical structure of PPE-NEt$_3$-OR11.
Figure 6:
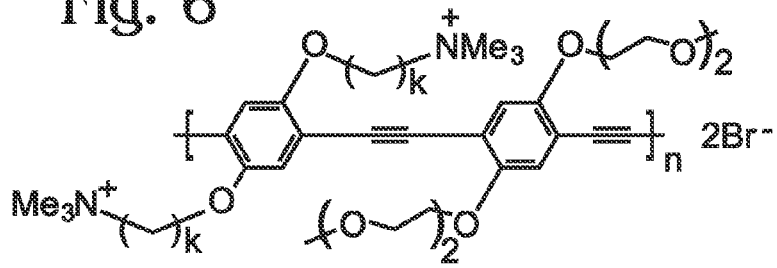
FIG. 6 is the chemical structure of PPE-NMe$_3$-OR8.
Figure 13:
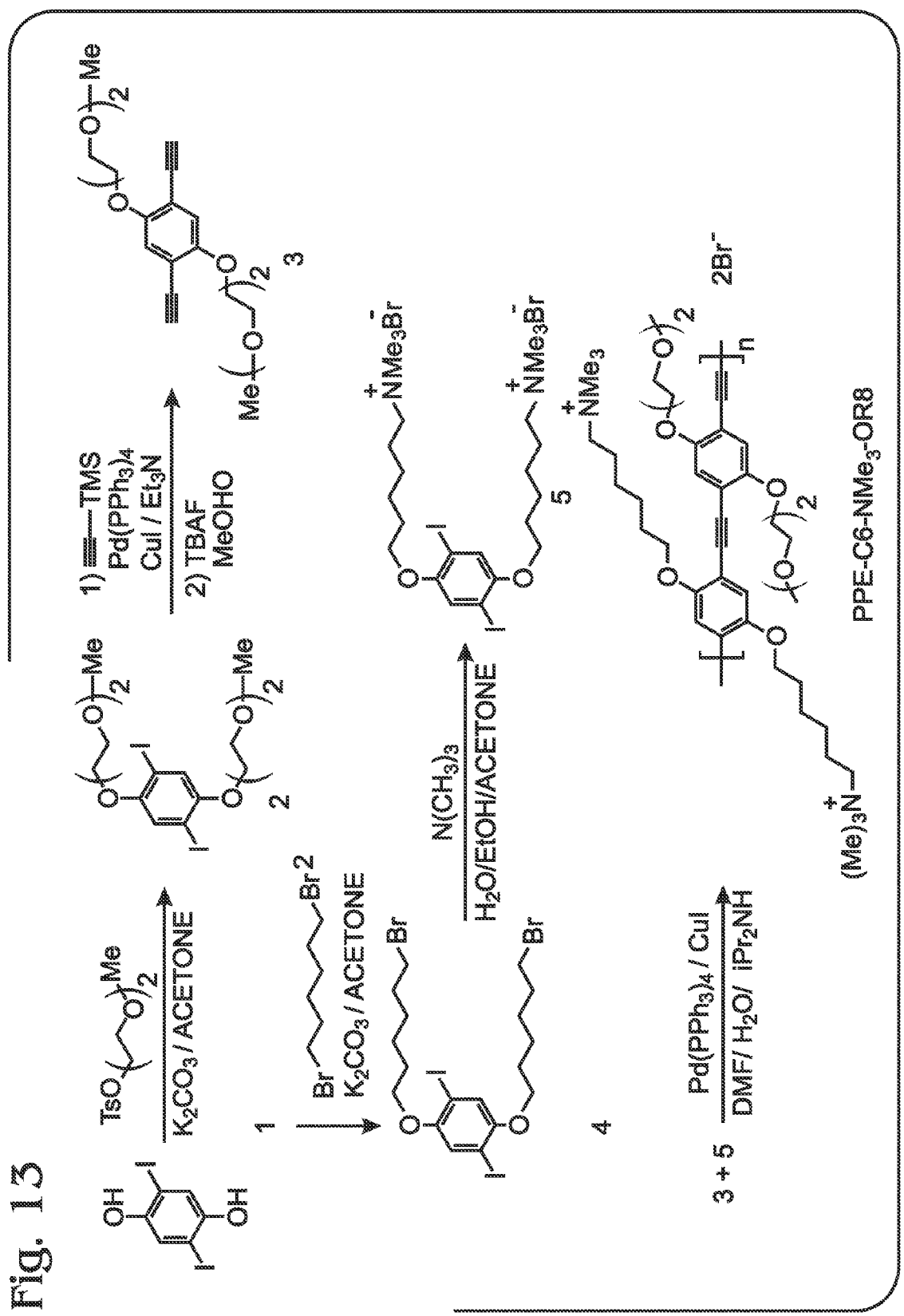
FIG. 13 is a schematic illustration of the synthesis scheme for PPE-Net$_3$-OR11 and PPE-NMe$_3$-OR8.

FIG. 5 shows the chemical structure of PPE-Net$_3$-OR11. Suitable counter ions for PPE-NEt$_3$-OR11 include Cl$^-$, Br$^-$ or I$^-$. FIG. 6 shows the chemical structure of PPE-NMe$_3$-OR8. Suitable counter ions for PPE-NMe$_3$-OR8 include Cl$^-$, Br$^-$ or I$^-$. An exemplary synthesis scheme for PPE-Net$_3$-OR11 and PPE-NMe$_3$-OR8 where k=3 is shown in FIG. 13. Synthesis for the scheme shown in FIG. 13 is as described below:

2,5-Diiodohydroquinone2 (1), 1,4-diiodo-2,5-bis[2-[2-(2-methoxyethoxy)ethoxy]ethoxy]benzene (2b), 1,4-diethynyl-2,5-bis[2-[2-(2-methoxyethoxy)ethoxy]ethoxy]benzene (3b), 1,4-bis(3-bromopropoxy)-2,5-diiodobenzene4 (4), and 3,3'-[(2,5-diiodo-1,4-phenylene)bis(oxy)]bis[N,N,N-trimethyl-1-propanaminium]bromide salt (5a), were synthesized according to the procedures described in Zhao, X. Y.; Pinto, M. R.; Hardison, L. M.; Mwaura, J.; Muller, J.; Jiang, H.; Witker, D.; Kleiman, V. D.; Reynolds, J. R.; Schanze, K. S. Macromolecules 2006, 39, 6355-6366, Tan, C. Y.; Pinto, M. R.; Schanze, K. S. Chem. Commun. 2002, 446-447, Ogawa, K.; Chemburu, S.; Lopez, G. P.; Whitten, D. G.; Schanze, K. S. Langmuir 2007, 23, 4541-4548, McQuade, D. T.; Hegedus, A. H.; Swager, T. M. J. Am. Chem. Soc. 20000, 122, 12389-12390, Nardello, V.; Azaroual, N.; Cervoise, I.; Vermeersch, G.; Aubry, J. M. Tetrahedron 1996, 52, 2031-2046. Unless otherwise noted, 1H and 13C NMR spectra were recorded on either a Varian Gemini 300, VXR 300, or Mercury 300 spectrometer, and chemical shifts are reported in ppm relative to TMS.

1,4-Diiodo-2,5-bis[2-(2-methoxyethoxy)ethoxy]benzene (compound 4a). 2,5-Diiodohydroquinone (compound 3) (5.79 g, 16 mmol), (2-Methoxyethoxy)ethyl tosylate (11.0 g, 40 mmol), and potassium carbonate (5.52 g, 40 mmol) were combined in a flask with 100 mL of acetone. The mixture was heated to 70° C. and kept stirring for overnight. The mixture was filtered and filtrate concentrated by rotary evaporation. Water was added and product was extracted with chloroform. The product was purified by column chromatography on silica using 2:3 mixture of ethyl acetate and hexane. Solvent was removed by rotary evaporation to give yellow oil. 1H NMR (300 MHz, CDCl3): δ 3.40 (s, 6H), 3.58 (m, 4H), 3.78 (m, 4H), 3.88 (m, 4H), 4.11 (m, 4H), 7.23 (s, 2H). 13C NMR (75 MHz, CDCl3): δ 59.5, 69.9, 70.7, 71.4, 72.4, 86.7, 123.8, 153.4.

1,4-diethynyl-2,5-bis[2-(2-methoxyethoxy)ethoxy] benezene (5a). Compound 4a (5.65 g, 10 mmol), trimethylsilylacetylene (3.1 mL, 22 mmol), CuI (57 mg, 0.3 mmol), and Pd(PPh3)4 (0.35 g, 0.3 mmol) were dissolved in 60 mL of THF and 40 mL of diisopropyl amine. Mixture was warmed to 70° C. and kept stirring overnight. Water was added and the mixture was extracted with ether followed by several washings with water. Solvent was removed in vacuo. The product was purified by column chromatography on silica using 1:4 mixture of ethyl acetate and hexane. Solvent was removed by rotary evaporation to give white solid.

The white solid was dissolved in 50 mL of methanol. To the solution, 50 mL of 1M NaOH(aq) was added and refluxed for 2 hours. Water was added to the mixture and extracted with ether. The organic layer was washed with water several times, then dried with Na2SO4. Solvent was removed by rotary evaporation to give reddish solid. The product was purified column chromatography on silica using at 2:3 mixture of ethyl acetate and hexane to give white solid after evaporation of the solvent. 1H NMR (300 MHz, CDCl3): δ 3.32 (s, 2H), 3.38 (s, 6H), 3.56 (m, 4H), 3.75 (m, 4H), 3.87 (m, 4H), 4.15 (m, 4H), 6.99 (s, 2H). 13C NMR (75 MHz, CDCl3): δ 59.4, 69.9, 69.9, 71.3, 72.4, 79.9, 83.1, 113.9, 118.6, 154.4.

3,3'-[(2,5-diiodo-1,4-phenylene)bis(oxy)]bis[N,N,N-triethyl-1-propanaminium]bromide salt (Compound 5b). Compound 4 (3.01 g 5 mmol) was suspended in a mixture of 100 mL of triethylamine, 38 mL of 4 water, 56 mL of ethanol, and 56 mL of acetone. The mixture was refluxed overnight. The solvent was evaporated and the residue was washed with acetone several times to yield white solid. 1H NMR (300 MHz, CD3OD): δ 1.30 (t, 12H), 2.16 (m, 4H), 3.33 (q, 8H), 3.45 (m, 4H), 4.04 (m, 4H), 7.30 (s, 2H). 13C NMR (75 MHz, CD3OD): δ 8.1, 23.3, 54.3, 55.9, 67.9, 87.2, 124.1, 154.1.

PPE-Net$_3$-OR11. Compound 3a (362 mg, 1 mmol), compound 5a (722 mg, 1 mmol), CuI (5.7 mg, 0.03 mmol), and Pd(PPh3)4 (35 mg, 0.03 mmol) were dissolved in a mixture of 30 mL of DMF, 20 mL of water, and 10 mL of diisopropylamine. The mixture was heated to 70° C. and kept stirring overnight. The reaction mixture was concentrated by rotary evaporation and added dropwise into 250 mL of acetone.

The precipitate was dissolved in a small amount of Millipore water and filtered through quantitative filter paper, followed by a 25 μm glass filter. The solution was dialyzed against water using 6-8 kD MWCO cellulose membrane. The solution was concentrated via rotary evaporation and the polymer was precipitated with acetone. The precipitate was collected by centrifugation and washed with acetone. The product was a bright yellow powder and it was dried under vacuum for 5 hours. 1H NMR (300 MHz, CD3OD): δ 2.46 (br), 3.05 (br), 3.14 (br), 3.44 (br), 3.60 (br), 3.79 (br), 4.16 (br), 7.16 (br).

PPE-NMe$_3$-OR8 was synthesized in a similar procedure using compound 3b (451 mg, 1 mmol), compound 5b (806 mg, 1 mmol) 1H NMR (300 MHz, CD3OD): δ 1.37 (br), 2.22 (br), 3.02 (br), 3.39 (br), 3.52 (br), 3.75 (br), 4.11 (br), 7.37 (br).

Figure 14:
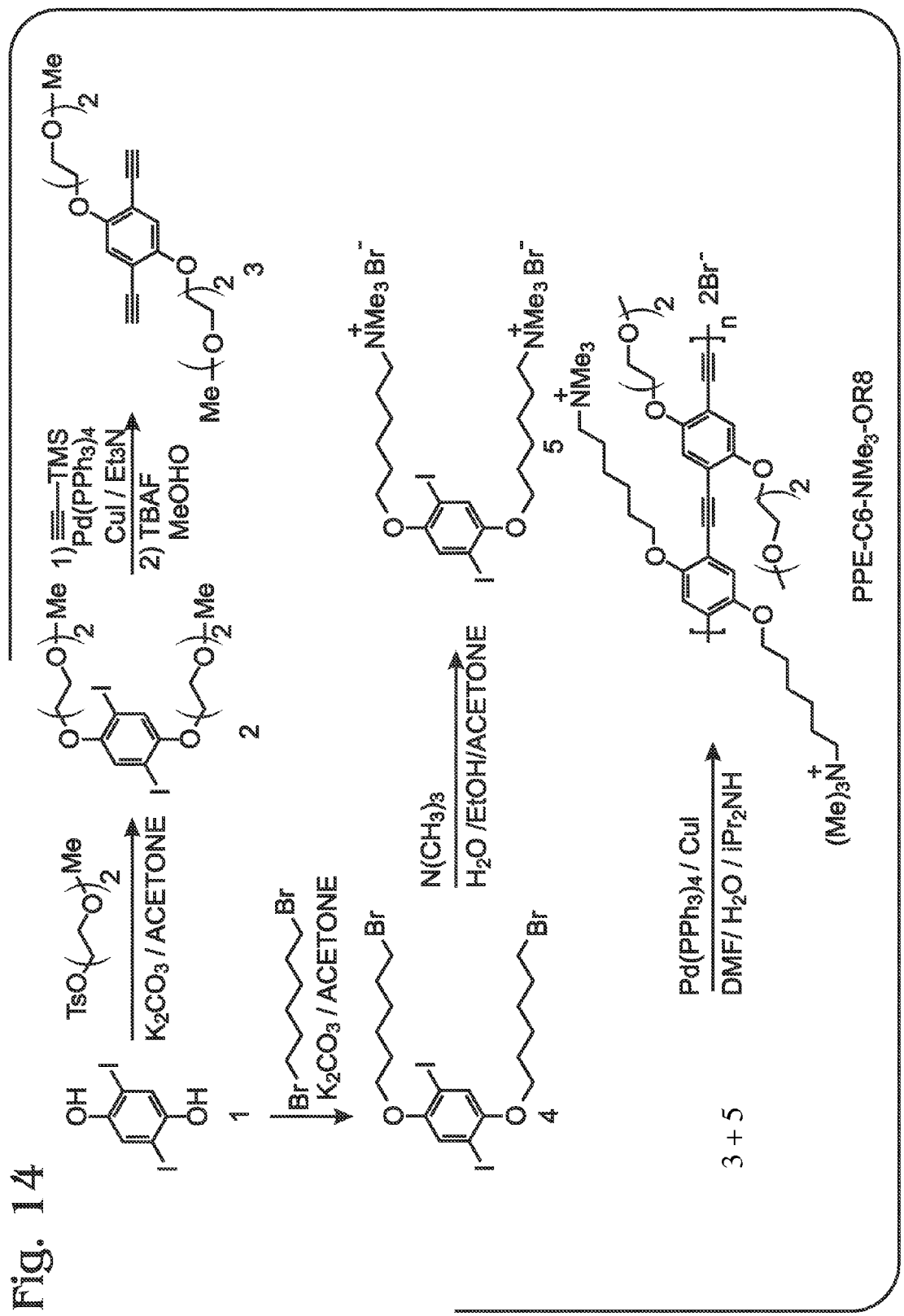
FIG. 14 is a schematic illustration of the synthesis scheme for PPE-C6-NMe$_3$-OR8.

As stated above, structures having various repeat units in the side chains are contemplated by the present disclosure. Accordingly, an exemplary synthesis scheme for PPE-C6-NMe$_3$-OR8 (FIG. 5) where k=6 (also referred to as PPE-C6-NMe$_3$-OR8) is shown in FIG. 14. Synthesis for the scheme shown in FIG. 14 is as described below:

Compound 2. 2,5-Diiodohydroquinone (2.00 g, 5.53 mmol) and diethylene glycol monomethyl ether p-toluenesulfonate (6.07 g, 22.12 mmol) in 120 mL of methylethylketone was placed under argon. To this solution K2CO3 (3.06 g, 22.12 mmol) and KI (0.09 g, 0.55 mmol) was added. The reaction mixture was refluxed at 100° C. for 48 hours and then cooled to room temperature. The solvent was removed and the solid was dissolved in CH2Cl2 (200 mL), followed by washing with 100 mL of 10% KOH solution, water, and saturated NaCl solution. The organic layer was dried with sodium sulfate and concentrated to give a gold color oil. Flash chromatography on silica gel (80% CH2Cl2/10% hexane/10% ethyl acetate) yielded a white solid (1.35 g, 43%). 1H NMR (300 MHz, CDCl3): δ 3.40 (s, 6H), 3.58 (m, 4H), 3.78 (m, 4H), 3.88 (m, 4H), 4.11 (m, 4H), 7.23 (s, 2H). 13C NMR (75 MHz, CDCl3): δ 59.5, 69.9, 70.7, 71.4, 72.4, 86.7, 123.8, 153.4.

Compound 3. Schlenk flask equipped with compound 2 (1.29 g, 2.27 mmol), CuI (0.013 g, 0.068 mmol), and Pd(PPh3)4 (0.052 g, 0.045 mmol) was placed under argon. And then 20 mL of toluene and 40 mL of diisopropylamine were added and argon bubbled through the solution for 30 minutes. To this solution, (trimethylsilyl)acetylene was added and the solution stirred at 70° C. for 3 days. The solvent was removed and the residue was dissolved in CH2Cl2 and filtered through one-inch silica gel using ethyl acetate. The filtrate was concentrated and purified by flash chromatography on silica gel (8% CH2Cl2/67% hexane/25% ethyl acetate) to yield a gold oil, which solidified slowly at room temperature (0.87 g, 76%). A two-necked flask with obtained compound (0.8 g, 1.58 mmol, 1 eq.) and methanol (45 mL) was placed and argon bubbled through the solution for 30 minutes. Tetrabutylammonium fluoride (1M in THF, 3.79 mL) was then added to the flask under the argon and the mixture was stirred at room temperature for 9 hours. The solvent was removed and the solid was purified by flash chromatorgraphy on silica gel (5% methanol/95% methylene chloride) to yield a light yellow solid (0.42 g, 1.16 mmol, 73%). 1H NMR (300 MHz, CDCl3): δ 3.32 (s, 2H), 3.39 (s, 6H), 3.55 (m, 4H), 3.74 (m, 4H), 3.86 (t, 4H), 4.15 (t, 4H), 7.00 (s, 2H). 13C NMR (75 MHz, CDCl3): δ 59.4, 69.9, 69.9, 71.3, 72.4, 79.9, 83.1, 113.9, 118.6, 154.4.

Compound 4. 1,6-dibromohexane (5.66 g, 23.22 mmol), K2CO3 (5.35 g, 38.7 mmol), and acetone (150 mL) were added to a three-neck, round bottomed flask equipped with a condenser and an additional flask. 2,5-Diiodohydroquinone (1.4 g, 3.87 mmol) was dissolved in 150 mL of acetone and added dropwise to the mixture solution at 70° C. The reaction was stirred overnight and cooled to room temperature. K2CO3 was removed by filtration through Celite and the solvent was removed. The resulting solid was dissolved in chloroform and washed with 10% NaOH, water, and saturated NaCl solution. The organic layer was dried with sodium sulfate, filtered and concentrated. The resulting solid was crystallized from ethylacetate and hexane. The white solid was dissolved in hot ethanol and insoluble solid was removed using hot filtration. The solution was concentrated to yield a white solid (yield 80%). 1H NMR (300 MHz, CDCl3): δ 1.52 (m, 8H), 1.87 (m, 8H), 3.41 (t, 3H), 3.92 (t, 4H), 7.17 (s, 1H).

Compound 5. Compound 4 (1.70 g, 2.47 mmol) was suspended in 25% trimethylamine in water (80 mL), ethanol (120 mL), and acetone (120 mL) and heated to 120° C. The reaction was refluxed overnight. The solvent was removed and the white solid recrystallized from ethanol to yield 91%. 1H NMR (300 MHz, CD3OD): δ 1.36 (m, 12H), 1.72 (m, 4H), 3.06 (s, 18H), 3.26 (m, 4H), 3.89 (t, 4H), 7.21 (s, 1H).

PPE-C6-NMe3-OR8 (16). Compound 3 (50.4 mg, 0.1 mmol) and compound 5 (109.2 mg, 0.1 mmol), DMF (5 mL), and water (5 mL) were placed into a Schlenk flask and degassed with argon for 30 min. In a separate flask, CuI (1 mg, 0.005 mmol), Pd(PPh3)4 (4.8 mg, 0.004 mmol), DMF (2.5 mL), and triethylamine (2.5 mL) were degassed with argon for 30 minutes and added to the degassed solution containing compound 5 and compound 10. The reaction mixture was stirred at 60° C. for 22 hours. The DMF solution was added to 200 mL of acetone to form a precipitate. The collected yellow precipitate was dissolved in an aqueous solution containing NaCN, filtered using a 25 μm glass filter, and followed by dialysis against deionized water using 6-8 kD MWCO cellulose membrane for 2 days. The polymer solution was lyophilized to yield a yellow solid (Yield: 63 mg, 49%). 1H NMR (300 MHz, DMSO-d6): δ 1.37 (br, 18H), 3.05 (s, 18H), 3.22 (s, 6H), 3.30 (br, 4H) 3.45 (br, 4H), 3.67 (br, 4H), 3.81 (br, 4H) 4.08 (br, 4H), 4.22 (br, 4H) 7.15 (br, 4H).

Figure 7:
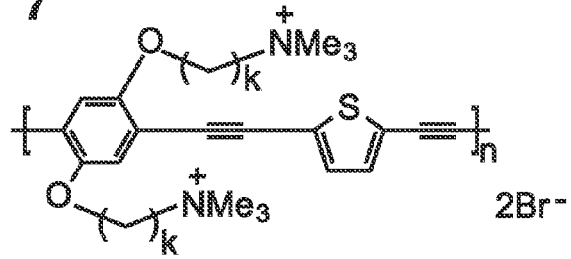
FIG. 7 is the chemical structure of PPE-NMe$_3$-Th.
Figure 15:
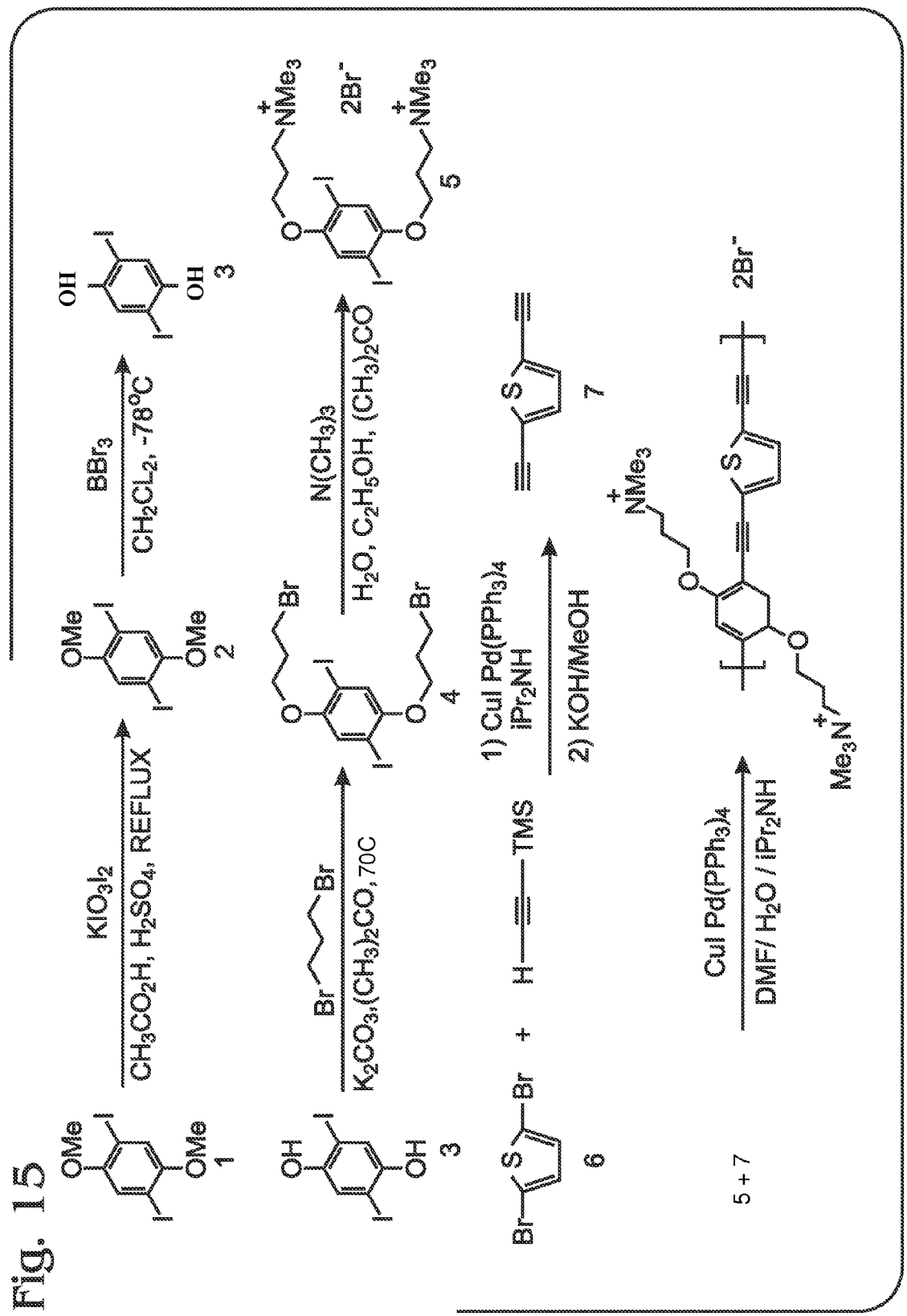
FIG. 15 is a schematic illustration of the synthesis scheme for PPE-NMe$_3$-Th.

FIG. 7 shows the chemical structure of PPE-NMe$_3$-Th. Suitable counter ions for PPE-NMe$_3$-Th include Cl$^-$, Br$^-$ or I$^-$. An exemplary synthesis scheme for PPE-NMe$_3$-Th where k=3 is shown in FIG. 15. Synthesis for the scheme shown in FIG. 15 is as described below:

Diiodohydroquinone (compound 3) 1,4-bis(3-bromopropoxy)-2,5-diiodbenzene (compound 4) and 3,3'-[(2,5-diiodo-1,4-phenylene)bis(oxy)]bis[N,N,N-trimethyl-1-propanaminium] bromide salt (compound 5) were synthesized according to the literature procedures as described in Zhou, Q.; Swager, T. M. J. Am. Chem. Soc., 1995, 117, 7017-7018, McQuade, D. T.; Hegedus, A. H.; Swager, T. M. J. Am. Chem. Soc. 2000, 122, 12389-12390, and Ogawa, K.; Chemburu, S.; Lopez, G. P.; Whitten, D. G.; Schanze, K. S. Langmuir, 2007, 23, 4541, respectively.

2,5-Bis(trimethylsilyl)ethynyl)thiophene (compound 6). 2,5-Dibromothiophene (4.00 g, 16.53 mmol), (compound 6) CuI (0.38 g, 1.98 mmol), Pd(PPh3)2Cl2 (0.69 g, 0.98 mmol), and 120 mL of isopropylamine were placed in a Schlenk flask and the solution was degassed with stirring for 30 min under ice-bath by bubbling argon gas. To this solution was added (trimethylsilyl)acetylene (6.49 g, 66.12 mmol). The solution was stirred under an icebath for 1 h. The temperature was raised to room temperature and mixture was kept stirring for an additional hour. The resulting solution was heated to 75° C. and stirred for 20 h. The solvent was removed and the solid was purified by flash chromatography on silica gel with hexane to yield a yellow solid 7 (2.54 g, 55.5%). 1H NMR (300 MHz, CDCl3): δ 0.24 (s, 18H), 7.04 (s, 2H).

2,5-Diethynylthiophene (compound 7). To a suspension of compound 7 (0.4 g, 1.45 mmol) in deoxygenated methanol (20 mL) was added 0.1 mL of 0.5 M aqueous KOH solution. The mixture was stirred at room temperature under argon for 40 min. The solution was diluted with water (50 mL) and extracted with n-pentane (2×50 mL). The combined organic solution was dried over Na2SO4 and the solvent removed at reduced pressure to yield 8 as a viscous oil (0.14 g, 73%). 1H NMR (300 MHz, CDCl3): δ 3.32 (s, 2H), 7.09 (s, 1H). 13C NMR (75 MHz, CDCl3): δ 132.6, 123.6, 82.1, 76.2.

PPE-NMe$_3$-Th. A solution of compound 5 (100 mg, 0.15 mmol), CuI (4 mg, 0.02 mmol), and Pd(PPh3)4 (10 mg, 0.01 mmol) in 8.5 mL of DMF/H2O/iPr2NH (v/v/v) 9/6/2) was deoxygenated with argon for 30 min. Then, compound 7 was added to the solution under argon. The resulting solution was heated at 70° C. for 22 h. The reaction mixture was poured into 200 mL of acetone. The precipitate was dissolved in small amount of Millipore water and treated with NaCN, filtered using 25 μm glass filter and followed by dialysis against deionized water using 6-8 MWCO cellulose membrane. The polymer solution was lyophilized to yield a yellow-tan solid (46 mg, 51%). 1H NMR (300 MHz, CD3OD): 2.38 (br), 3.21 (br), 3.63 (br), 4.22 (br), 7.23 (br), 7.33 (br). 13C NMR (75 MHz, CDCl3) spectrum was not obtained due to the limited solubility of the compound.

Figure 8:
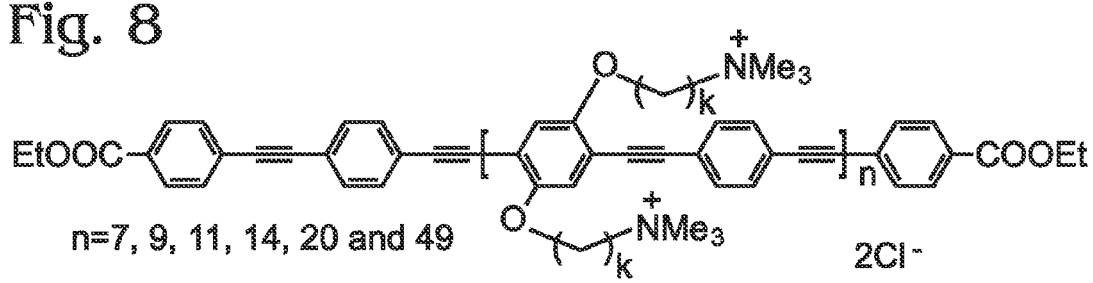
FIG. 8 is the chemical structure of PPE-NMe$_3$-n-COOEt.
Figure 10:
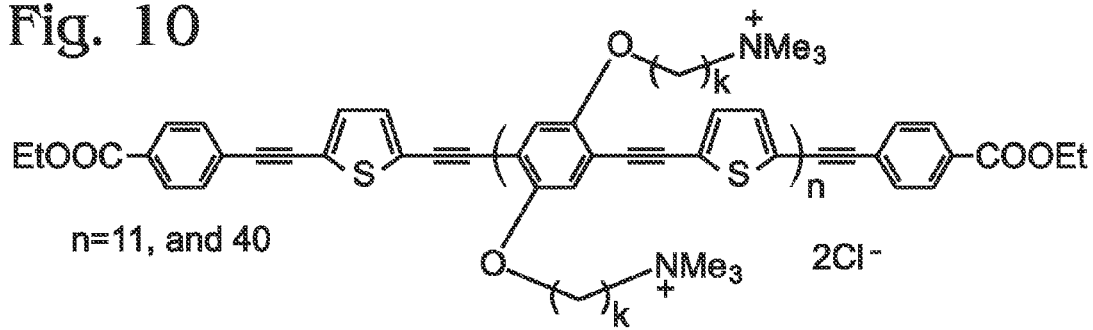
FIG. 10 is the chemical structure of PPF-NMe$_3$-Th-n-COOEt.
Figure 16:
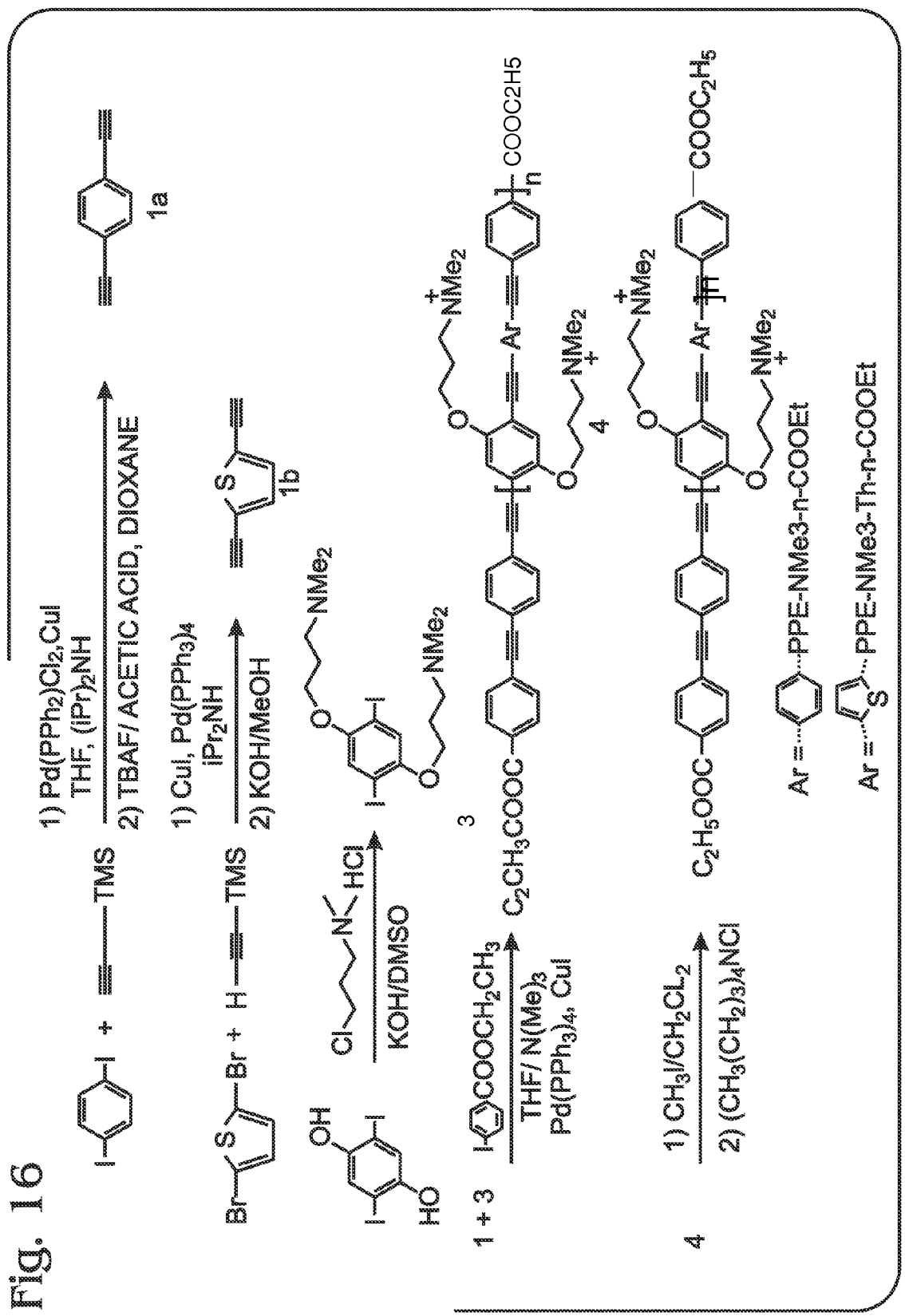
FIG. 16 is a schematic illustration of the synthesis scheme for PPE-NMe$_3$-n-COOEt and PPE-NMe$_3$-Th-n-COOEt.

FIG. 8 shows the chemical structure of PPE-NMe$_3$-n-COOEt. Suitable counter ions for PPE-NMe$_3$-n-COOEt include Cl$^-$, Br$^-$ or I$^-$. FIG. 10 shows the chemical structure of PPE-NMe$_3$-Th-n-COOEt. Suitable counter ions for PPE-NMe$_3$-Th-n-COOEt include Cl$^-$, Br$^-$ or I$^-$. An exemplary synthesis scheme for PPE-NMe$_3$-n-COOEt and PPE-NMe$_3$-Th-n-COOEt where k=3 is shown in FIG. 16. Synthesis for the scheme shown in FIG. 16 is as described below:

Monomer 1 (1.0 mmol), monomer 3 (1.0 mmol), and a specific amount of ethyl-4-iodobenzoate (varying from 10 to 55 molar percent) were dissolved in the solvent mixture (40 mL) of THF/Et$_3$N (v/v=3/2) in a Schlenk flask. The solution was degassed with argon for 30 minutes at 55° C. and followed by the addition of CuI (10 mg, 0.052 mmol) and Pd(PPh$_3$)$_4$ (32 mg, 0.028 mmol). The reaction mixture was stirred under argon at 60° C. for 24 hours. The reaction mixture was poured into 400 mL of methanol. The precipitate was collected by vacuum filtration and further purified by one repeated cycle of dissolution in THF or chloroform and precipitation in methanol. The organic soluble polymers were quaternized according to the procedure described in Tang, Y. L.; Zhou, Z. J.; Ogawa, K.; Lopez, G. P.; Schanze, K. S.; Whitten, D. G. *Langmuir* 2009, 25, 21. The quaternized polymers was further purified by filtration through a 25 μm glass filter and dialysis against deionized water using 3.5 or 12 kD (depending on the number of polymer repeat units) molecular weight cutoff (MWCO) cellulose membrane for 2 days.

Figure 9:
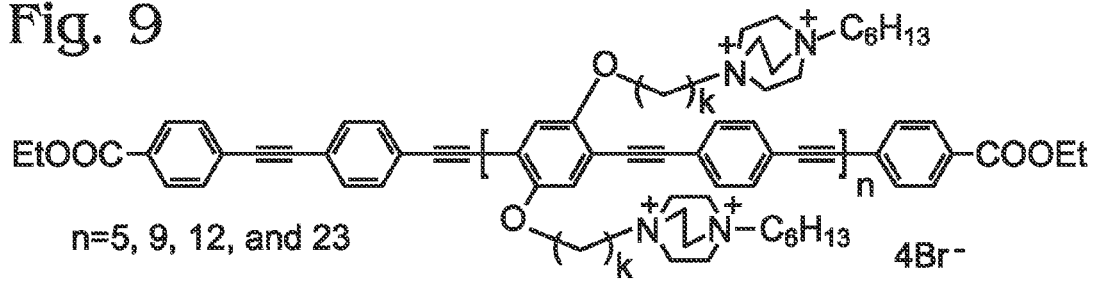
FIG. 9 is the chemical structure of PPE-DABCO-n-COOEt.
Figure 17:
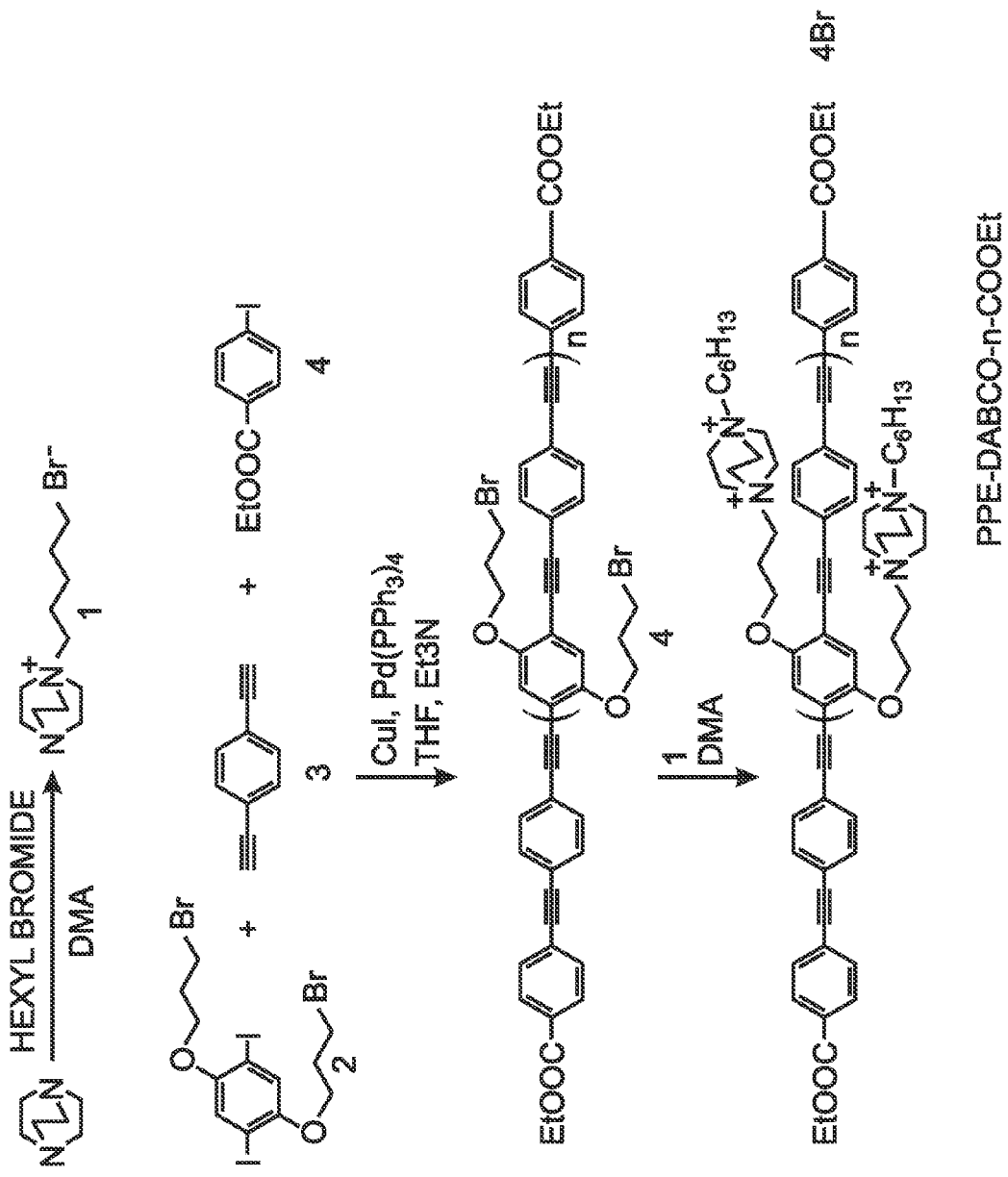
FIG. 17 is a schematic illustration of the synthesis scheme for PPE-DABCO-n-COOEt.

FIG. 9 shows the chemical structure of PPE-DABCO-n-COOEt. Suitable counter ions for PPE-DABCO-n-COOEt include Cl$^-$, Br$^-$ or I$^-$. An exemplary synthesis scheme for PPE-DABCO-n-COOEt where k=3 is shown in FIG. 17. Synthesis for the scheme shown in FIG. 17 is as described below:

Monomer 2 (1.0 mmol), monomer 3 (1.0 mmol), and a specific amount of ethyl-4-iodobenzoate (4, varying from 10 to 30 molar percent) were dissolved in the solvent mixture (20 mL) of THF/Et$_3$N (v/v=3/2) in a Schlenk flask. The solution was degassed with argon for 30 minutes at room temperature and followed by the addition of CuI (10 mg, 0.052 mmol) and Pd(PPh$_3$)$_4$ (32 mg, 0.028 mmol). The reaction mixture was stirred at room temperature under argon for 24 hours. The reaction mixture was poured into 400 mL of methanol. The precipitate was collected by vacuum filtration and further purified by one repeated cycle of dissolution in THF or chloroform and precipitation in methanol. A solution of compound 1 (0.25 mmol) in 1 mL of DMA was added to the organic soluble polymer (0.1 mmol) solution in 3 mL of DMA. The mixture solution was stirred at 60° C. for 24 h. The resulting solution was poured into 100 mL of acetone. The obtained solid polymers containing diazabicyclooctane (DABCO) based alkylammonium groups (PPE-DABCO-n-COOEt) was collected by vacuum filtration and dissolved in deionized water. The polymers were further purified by filtration through a 25 μm glass filter and dialysis against deionized water using 3.5 or 12 kD (depending on the number of polymer repeat units) molecular weight cutoff (MWCO) cellulose membrane for 2 days.

Each of the PPEs described herein has been tested for and has demonstrated significant dark and light-induced biocidal activity. An exemplary study is shown and described in Examples I and II, below. (Furthermore, at least some of the PPEs described herein may have the ability to retain activity even during photobleaching, as shown in Example V, below.) Accordingly, in yet another embodiment, the present disclosure provides novel biocides formed from or otherwise incorporating the PPEs described herein. Penetration of the bacterial membrane and binding of PPEs with DNA may provide paths for this activity. Further studies have shown that while PPEs are structurally diverse, they are generally amphiphilic due to the hydrophilic, charged side chains positioned along the rod-like hydrophobic PPE backbone. Dye leakage studies demonstrated a size dependent membrane perturbation against bacterial membrane mimics, with longer oligomers exhibiting higher activity than their smaller counterparts. Furthermore, the membrane perturbation activity appears to be selective with respect to specific types of membrane lipids—that is, most PPEs perturbed bacterial but not mammalian membrane mimics, providing specificity that enables them to be used in a variety of environments, including those in which mammalian cells are present.

Furthermore, a number of the PPEs described herein (and all of those that were tested) demonstrated significant antiviral activity, as shown in Example II, below. Accordingly, in yet another embodiment, the present disclosure provides novel antivirals formed from or otherwise incorporating the PPEs described herein.

Moreover, as shown in Example IV, below, PPE-DABCO has demonstrated significant antifungal activity. It is reasonable to assume that PPE-DABCO-n-COOEt would also have significant antifungal activity.

Accordingly, the PPEs disclosed herein are able to interfere with the pathogenicity a wide variety of pathogens, by inactivating, killing, or otherwise harming them. Thus, the PPEs described herein are suitable for attachment to, incorporation in, or association with a wide variety of substances and materials in order to prevent, reduce, or eliminate pathogens and pathogen-related harm caused to or by the substances and materials.

For example, the PPEs disclosed herein are suitable for attachment to or formation of fibrous or other materials in order to produce textiles or other (soft or hard) surfaces having antimicrobial, antiviral and/or antifungal properties. Thus, according to various embodiments, it may be desirable to have one or more of the PPEs disclosed herein functionally and robustly attached to a surface, for example via covalent linkages so that it can interfere with the pathogenicity of any pathogen the PPE comes into contact with. According to some embodiments, attachment of the PPE via chemisorption and physisorption may also be used.

In chemisorptions, a textile substrate is chemically activated with a primer or initiator and then reacted with a polymer or prepolymer to graft the conjugated polyelectrolyte to the surface in a step growth polymerization process.

Figure 18:
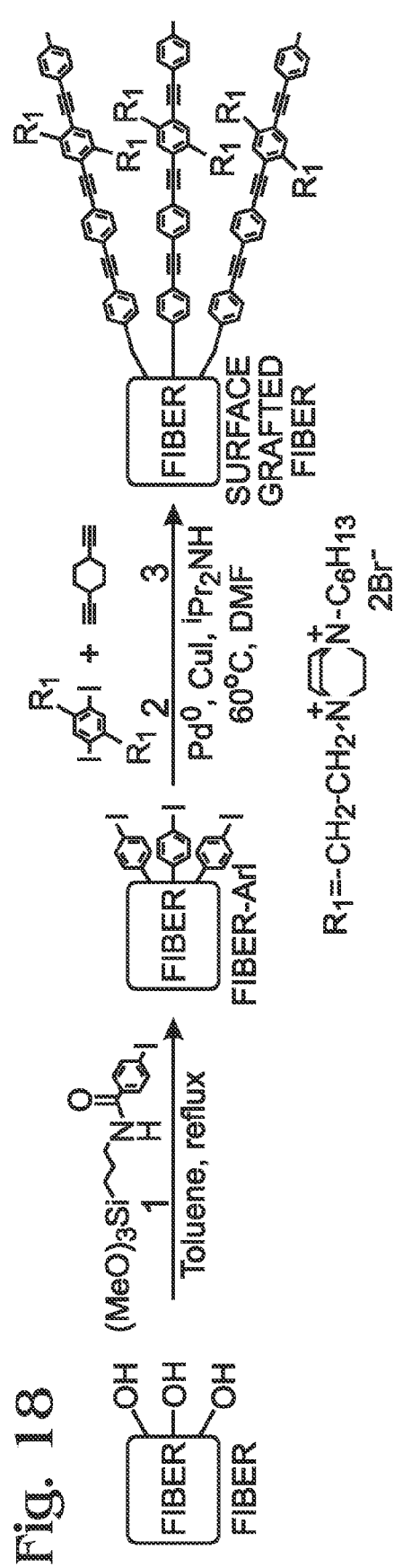
FIG. 18 shows an exemplary chemisorption scheme employing a step growth polymerization process.

An exemplary chemisorption scheme employing a step growth polymerization process is shown in FIG. 18. Alternate reaction schemes may employ a living polymerization mechanism utilizing molecule by molecule propagation starting from a single molecule initiator.

In physisorption, the textile and conjugated polyeletrolyte are mixed under appropriate conditions such that the positively charged polymer attaches to the negatively charged textile surface. Typically the PPE is dissolved in a solvent (e.g., water or methanol) and the fabric is "dyed" with the solution.

Alternatively, according to still an embodiment, an initial organosilane attachment may be used as a synthetic approach to accomplish surface grafting. See, e.g., Ogawa, K.; Chemburu, S.; Lopez, G. P.; Whitten, D. G.; Schanze, K. S. "Conjugated Polyelectrolyte-Grafted Silica Microspheres" Langmuir, 2007, 23, 4541-4548, which is hereby incorporated by reference. By putting an organic iodine on the substrate we have grafted PPEs on nano- and microparticles and planar surfaces. This silane approach may also be used to graft PPEs onto fabrics. Furthermore, this approach can be easily extended to provide more robust linkages than silanes, using modified chemistries for attaching PPEs to surfaces including ester, ether and amide linkages as needed.

Accordingly, the PPEs described herein may be incorporated into or onto hard or soft surfaces using the techniques described above or, alternatively, by other known casting, electrospinning, dipping, or coating techniques. However, it is noted that the photophysical properties of PPEs are dependent on planarity which can be affected by self-assembly onto a substrate or placement in a poor solvent. Accordingly, these factors should be considered and taken into account when selecting a particular attachment or incorporation method.

As a still further embodiment, the PPEs may themselves be formed into fibers, for example via electrospinning.

It will be appreciated that any suitable fabric or material, including natural and/or synthetic fibers and materials may be used as an attachment surface for the PPEs described herein. According to some embodiments, suitable fabrics may comprise or consist of natural fibers such as cotton, silk and/or wool, or suitable blends thereof. Blended fabrics may include only natural fibers, only synthetic fibers, or both natural and synthetic fibers. In some cases, the antimicrobial polymers described herein may be incorporated into electrospun fibers for woven fabrics including, but not limited to filters. Other suitable textiles may include, but are not necessarily limited to rayon, nylon, or blends of cotton, silk, wool or other natural fabrics or fibers with synthetic fabrics or fibers of rayon or nylon.

Potential uses of fibers may include prophylaxes for potentially contaminated surfaces including mattresses and bed linens, countertop coverings, tablecloths, curtains and various swabs, bandages, sterile mats and liners for use both inside and outside a sterile/clinical environment or in food-preparation areas. Their uses may be directed against known contamination, as in a wound infection, or applied as a deterrent to propagation of pathogenic agents in such applications as coverings for common fomites. Treatments of the compounds onto various cellulosic components would also enable their use as filter elements for water purification.

Different blends to specifically release or retain killed bacteria could be developed based on combination of polymers with the desired retention properties. This could be effected either by use of varied polymer proportions in a single layer coating or by building multiple layers with the required external affinities.

According to some embodiments, the PPEs described herein may be incorporated into materials having commercial, industrial and/or household applications. Alternatively, the PPEs described herein may be used as or incorporated into antimicrobial, antivirial or antifungal coatings for such materials. For the purposes of this application, it should be noted that the term "material" incorporates both "soft" and "hard" substances including organic and inorganic matter such as, but not limited to, natural and man-made fabrics, plant-based materials, metals, polymers, wood, stone, plastic, and the like.

Examples of suitable medical applications for the PPEs described herein include bedsheets, hospital garments, curtains, floor and wall materials, air filtration systems, medical devices, bandages, surgical instruments, gloves, masks, lab coats, gauze orthopedic prostheses, bedding, bed frames, mattress covers, surgical furniture, dividers, curtains, carts for transport of medication, linens, dental trays, incise drapes, wound dressings, and implants.

Applications for the building industry include the coating or incorporation of PPEs in wall laminates, hand rails, pulls, trims, door handles, slings, hoists, window blinds, paints, sealants, polishes, and plastics.

Other applications include coatings for keyboards, gaining devices, toys, (for example, but limited to, in a daycare environment), industrial, commercial and household kitchens, food preparation equipment and utensils or any other surface where a sterile environment is desirable.

According to various embodiments, the PPEs described herein may be incorporated into various aspects of filtrations devices. For example, the antimicrobial polymers may be incorporated into filter elements for air filtration systems such as those used in commercial or residential buildings, cars, buses, trains airplane cabins etc. Alternatively or additionally, the antimicrobial polymers may be incorporated into commercial or household water or other liquid filtration systems by application of coatings on equipment and incorporation into and/or coating on filters. Alternatively or additionally, the antimicrobial polymers described herein may be utilized in recoverable bacterial absorbents (by filtration or magnetic components) in the form of coated beads or other suitable substrates. Furthermore, they may be incorporated in separation membranes for bacterial exclusion, extraction, and/or immobilization. They may also be incorporated into or used as a coating for disposal bags for biological waste or other (potentially) contaminated materials.

Other applications include in-can or in-tank preservation of aqueous functional fluids. This may include incorporation of the presently described PPEs into polymer emulsions, paints and coatings, adhesives and sealants, mineral slurries, metal working fluids, cosmetics and personal care products and cooling and recreational water. (See, e.g., Bruns et al. "Directory of Microbiocides for the protection of materials: A Handbook Chapter 3 R&D in material protection: new biocides," Wilfried Paulus, Ed.; Springer (2005).

Specific combinations and directed multilayer constructs may lend themselves to either single use or multiple uses, depending on the sequestration properties of that given combination. For example, coatings that have a high affinity for microbial binding may lend themselves more to single use applications (i.e. bandages or wipes) and those that would release microbial material, either upon washing or other decontamination could undergo multiple uses (i.e. bed linens, tablecloths).

According to various embodiments, the PPEs disclosed herein may be used to form or otherwise incorporated into gels or other materials. These gels or other materials may further include other biologically active materials. Much recent work has been devoted to the development of materials whose properties can be altered drastically by relatively small changes in properties such as temperature, pressure, solution or suspension properties (including but not limited to pH); these "stimuli responsive materials" (SRM) are often prepared as polymers or as surfaces prepared from components that can be covalently linked or self-assembled on surfaces. Smart polymers that have found use in biotechnology and medicine have been described by I Yu Galaev in Russian Chemical Reviews 64: 471-489 (1995); A. S. Hoffman in Clinical Chemistry 46:1478-1486 (2000) and H. G. Schild, Prog. Polym. Sci. 17, 163 (1992), incorporated herein by reference.

Prominent examples of SRMs include poly (N-isopropylacrylamide) (PNIPAAM) and oligo-ethylene glycol oligomer terminated with a thiol (OEG). The former can be grown from a surface by attaching an initiator monomer to a surface and following this with in situ polymerization. Through an ATRP process; the thickness of the resulting film can be controlled as a function of incubation time at a fixed catalyst and monomer concentration. The OEGs can be attached to a surface (usually Au) by covalent assembly as a self-assembled monolayer (SAM). For surfaces coated with either PNIPAAM or OEG there is a strong temperature dependence of the film properties. In both cases, films formed from these materials in contact with an aqueous solution exist as hydrated, expanded films at low temperatures that are relatively unreactive and non-adsorbtive towards various biological species including proteins, cells, bacteria, viruses, and the like. Above a specific lower critical solution temperature (LCST) the films contract, releasing water and become very hydrophobic. At temperatures higher than the LCST films from either SRM become thinner and strongly attract proteins, cells and other biological species that do not bind below the LCST.

According to yet another embodiment, the present disclosure provides films and assemblies containing both SRM components and the PPEs described herein. In general, these assembles provide a novel functional material that can be switched between active and inactive forms wherein, in the active form, the material is able to capture a biological species of interest and, in inactive form, the material is able to release the biological species. In some embodiments the material can be switched between active and inactive forms repeatedly, allowing for reuse of the same material. Films containing these two functional components can be readily prepared by covalent synthesis or by a self assembly process employing a mixture of individual SRM and PPE thiols.

Figure 19:
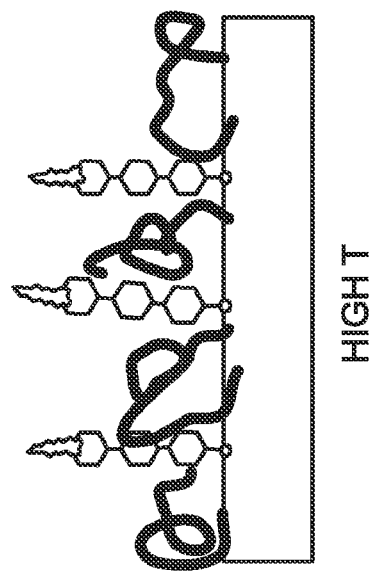
FIG. 19 show a PPE hidden amidst the expanded form of an SRM.
Figure 20:
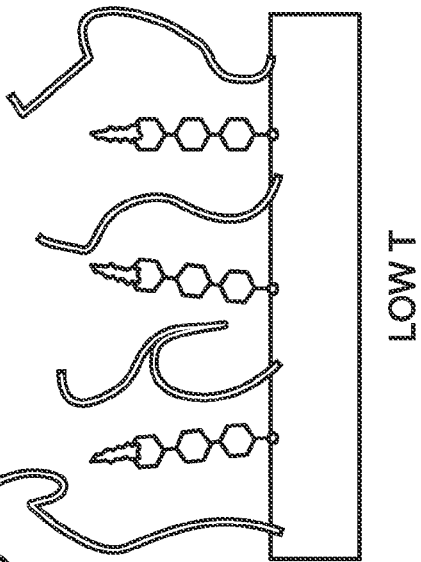
FIG. 20 shows a PPE unsheathed after exposure to a higher temperature.
Figure 21:
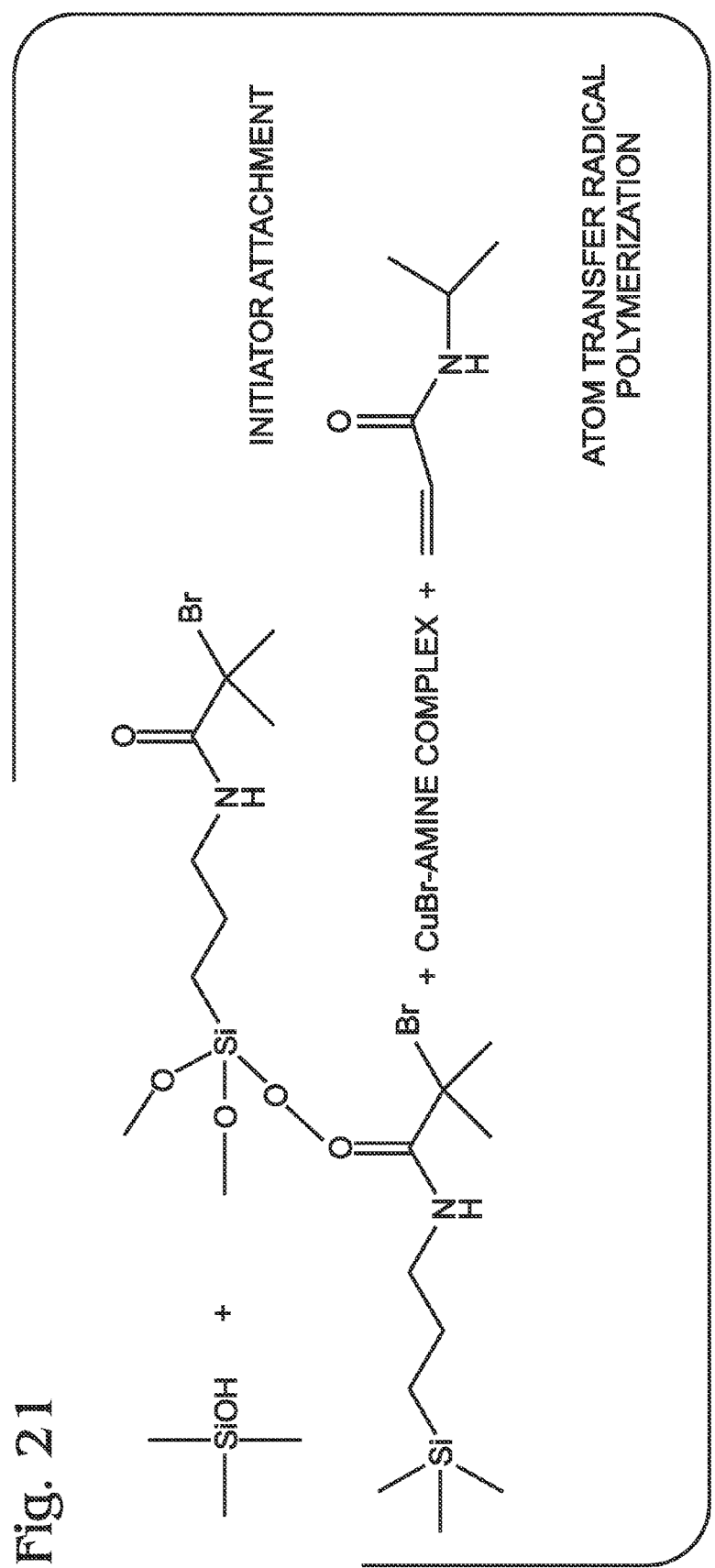
FIG. 21 depicts a method of synthesis of PNIPAAM by monomer polymerization onto an initiator functionalized surface.

Viewing FIG. 19 it can be seen that at low temperatures an PPE of appropriate length is buried amidst the expanded form of the SRM and inaccessible to any biological species (such as a protein, cell, bacteria, virus, etc.) present in the aqueous media. Moreover, these species are not attracted to the surface and do not associate with it. However, as the temperature is elevated above the LCST, contraction of the SRM component "unsheathes" the PPE, as shown in FIG. 20. Both components are now hydrophobic and strongly attractive. Accordingly, the unsheathed PPE is able to form a complex with the biological species.

Accordingly, in one embodiment, the presently described structure can form a reusable biocidal material. Under low temperatures the antimicrobial activity of the PPE is masked by the extended SRMs and therefore inactive. As stated above, elevation of the temperature above the LCST unsheathes the PPE, which is then allowed to form a complex with, thereby trapping, the bacteria. The PPE's biocidal activity is then exploited to inactivate, kill or destroy the trapped species, under either dark conditions or under uv light irradiation. Following destruction of the pathogen, the film will typically be contaminated with debris from the killed bacteria or cell. Returning the film to temperatures lower than the LCST results in expansion of the SRM, forcing the debris away from the PPEs. The result is a self-cleaning, reusable, biocidal film.

Examples of other practical uses for these mixed films include employing them as an active sensor which can be monitored by steady state fluorescence or by laser interferometery. The attachment of protein, cells or bacteria to the surface can be detected, for example, by the monitoring irradiation.

The present disclosure further provides methods of manufacturing the functional materials described herein. Thiol terminated OEG derivatives are commercially available in a wide range of structures. A method of synthesis of PNIPAAM by monomer polymerization onto an initiator functionalized surface is shown in FIG. 21.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

As used herein and in the appended claims, the singular forms "a," "an," and "the" include plural reference unless the context clearly dictates otherwise.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

EXAMPLES

Example I—Biocidal Activity of PPE-NMe3-n-COOEt

As described herein, we synthesized cationic CPEs (PPE-NMe3-n-COOEt, n=7, 9, 11, 14, 20, and 49) with variable chain lengths by controlling the added amount of a mono-functional "end-capping" agent, ethyl 4-iodobenzoate to the polymerization reaction.

Biocidal activity experiments were conducted under dark and light exposed conditions with two different concentrations (1 and 10 μM) of polymer solution. Two trends were found: (1) shorter chain length of polymers show stronger antimicrobial activity against *Escherichia coli* under both dark and light exposed conditions and (2) a higher concentration of polymer solution shows inner filter effect.

Figure 22:
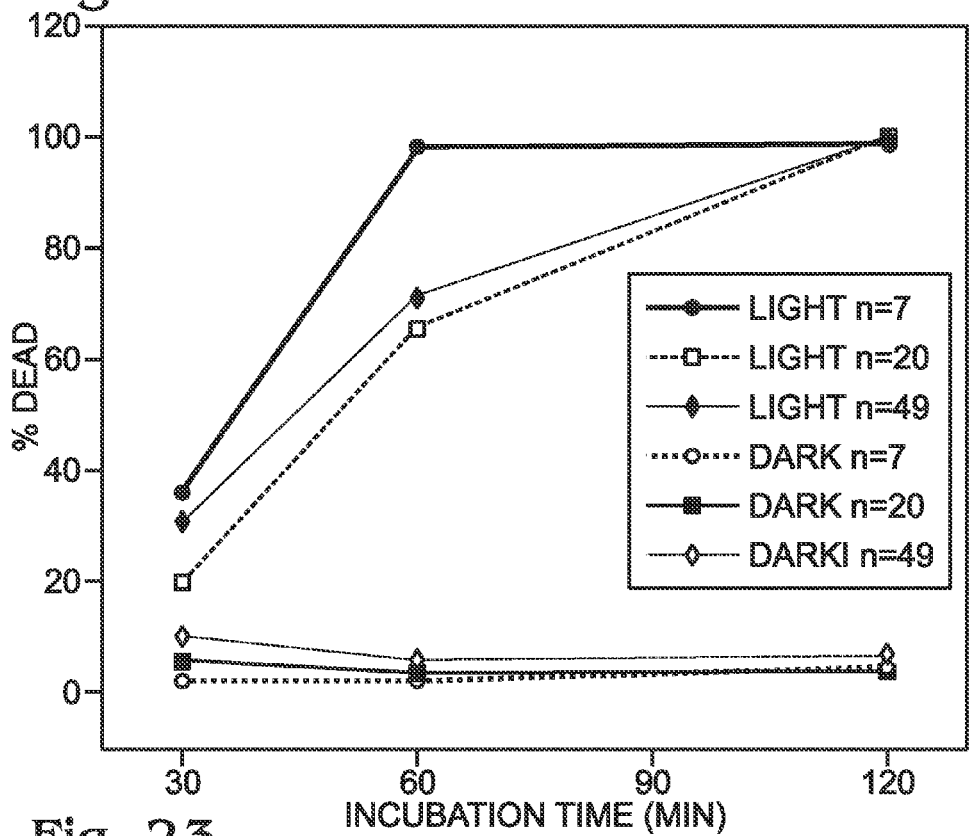
FIG. 22 is a plot of biocidal activity of the polymers against *Escherichia coli* (*E. coli*), where the concentration of the polymers was 1 ug/mL.
Figure 23:
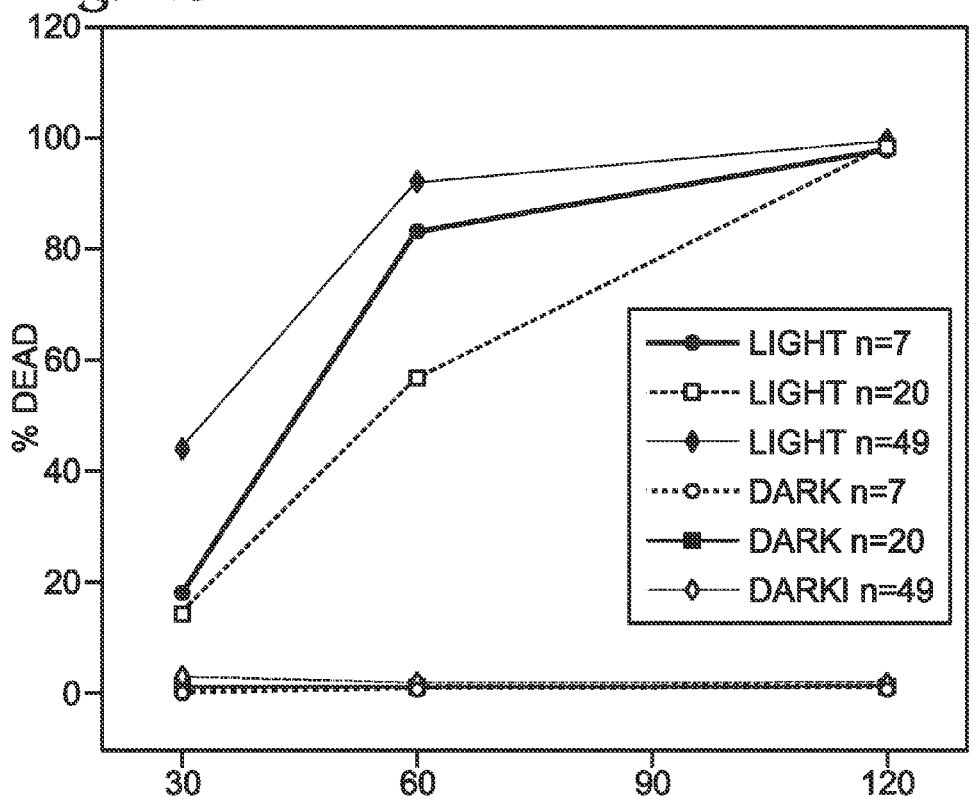
FIG. 23 is a plot of biocidal activity of the polymers against *Escherichia coli* (*E. coli*) where the concentration of the polymers was 10 ug/mL.
Figure 24:
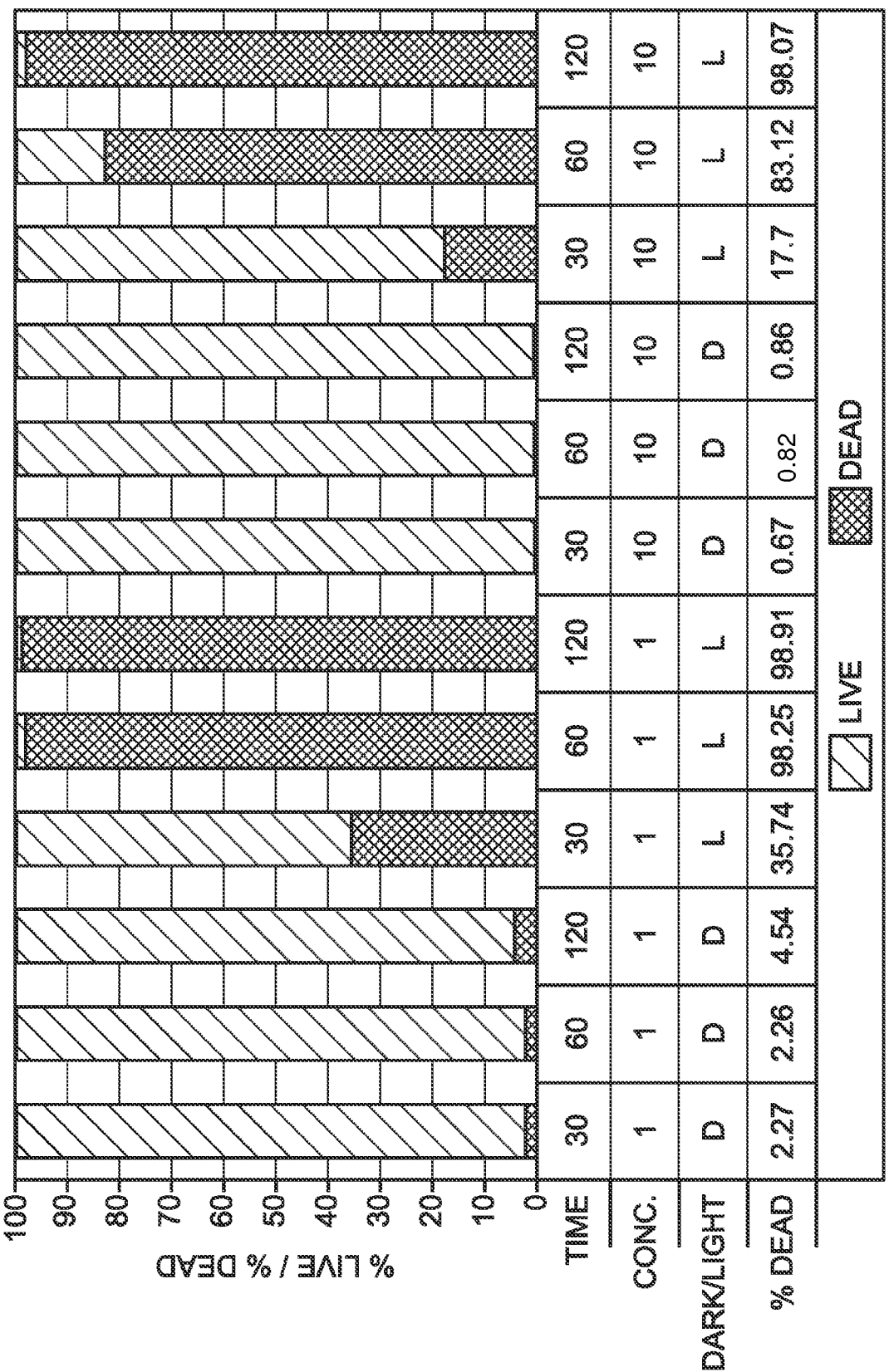
FIG. 24 shows the biocidal activity of the polymers as demonstrated by flow cytometry.
Figure 25:
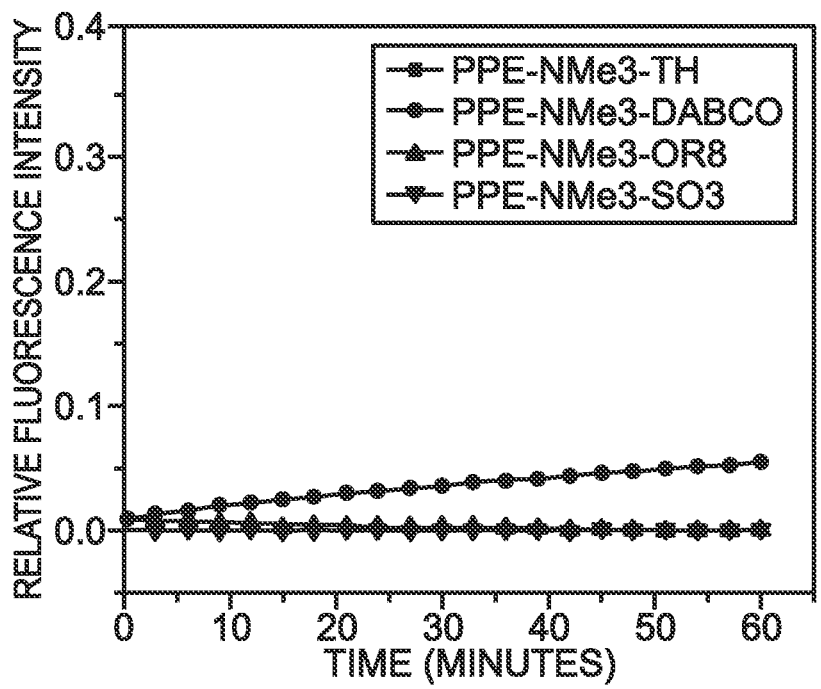
FIG. 25 is a graph of fluorescein leakage profiles from DOPC/cholesterol (67/33) vesicles with the addition of PPE-NMe3-Th, PPE-NMe3-DABCO, PPE-NMe3-OR8 and PPE-NMe3-SO3. Fluorescence from vesicles incubated alone was subtracted.
Figure 26:
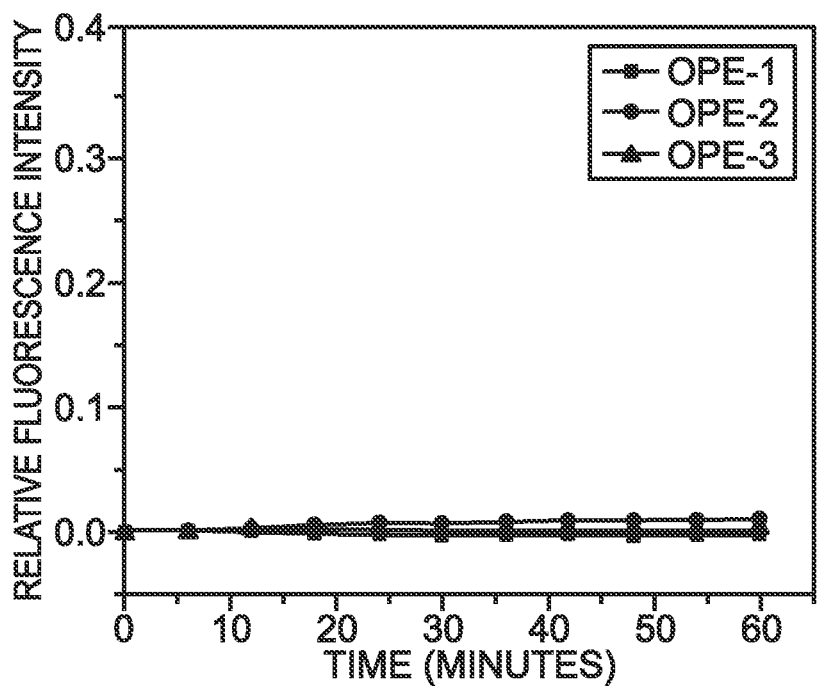
FIG. 26 is a graph of fluorescein leakage profiles from DOPC/cholesterol (67/33) vesicles with the addition of OPE-1, OPE-2 and OPE-3.
Figure 27:
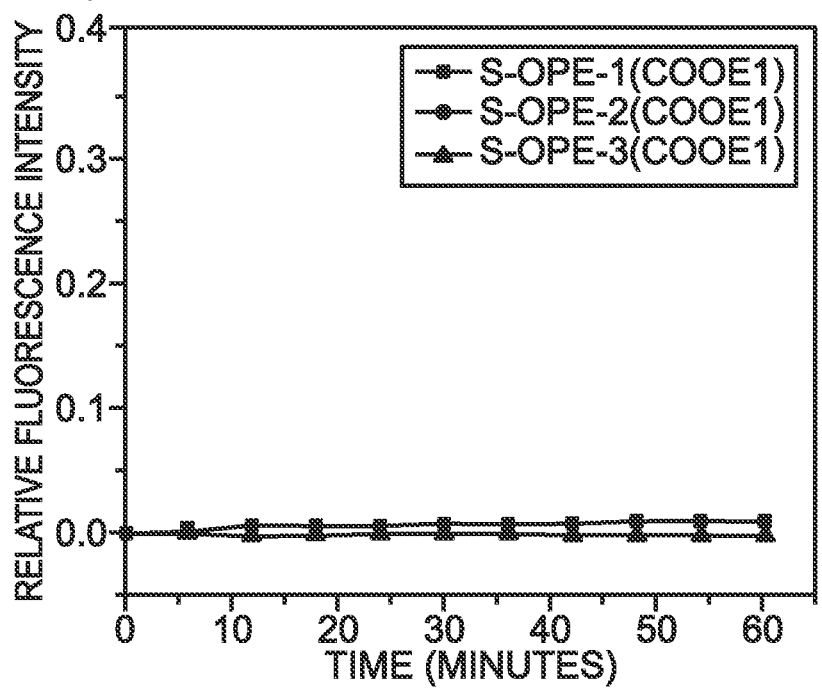
FIG. 27 is a graph of fluorescein leakage profiles from DOPC/cholesterol (67/33) vesicles with the addition of S-OPE-1(COOEt), S-OPE-2(COOEt), and S-OPE-3 (COOEt).
Figure 28:
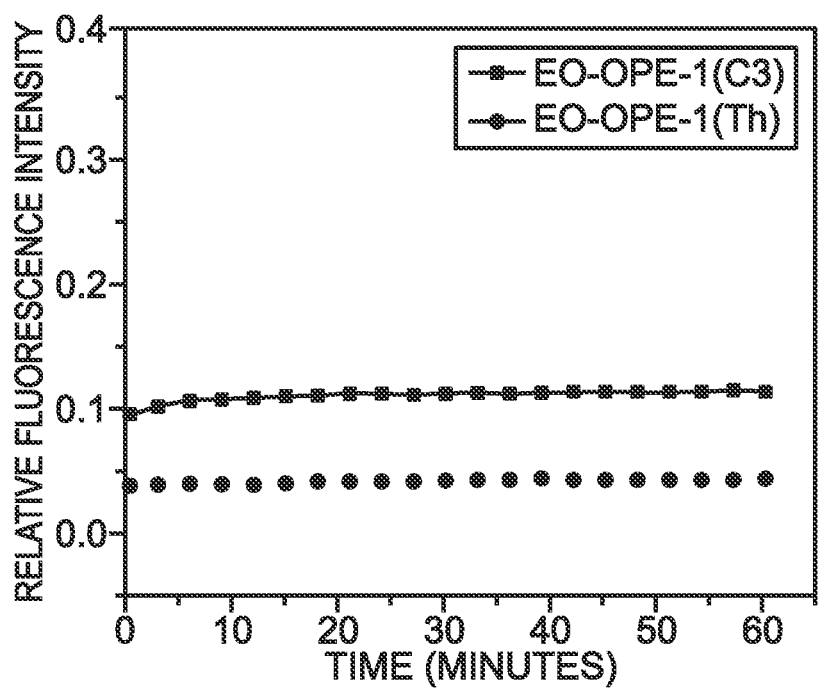
FIG. 28 is a graph of fluorescein leakage profiles from DOPC/cholesterol (67/33) vesicles with the addition of EO-OPE-1(C3) and EO-OPE-1(Th).
Figure 29:
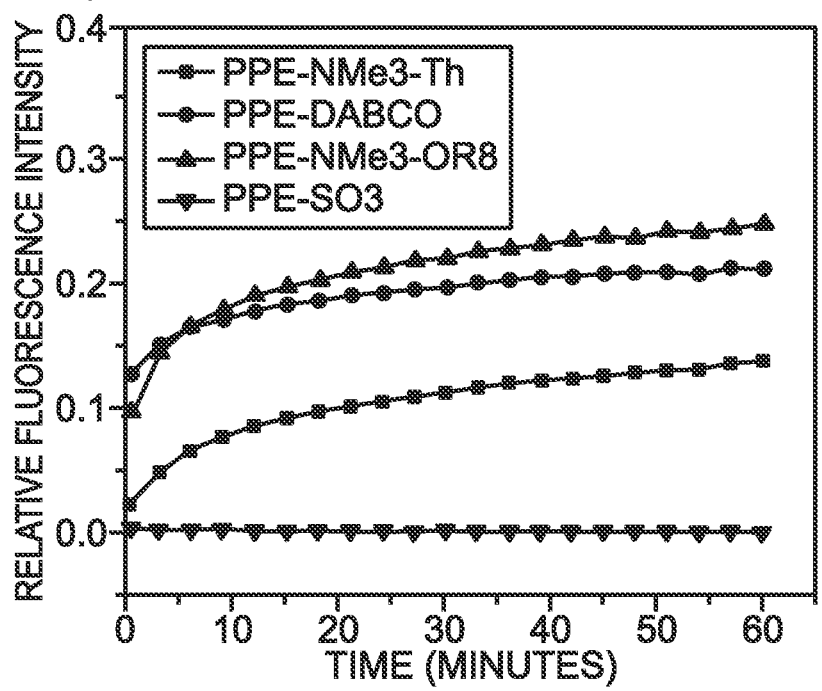
FIG. 29 is a graph of fluorescein leakage profiles from DOPG/DOPE (20/80) mixed vesicles with the addition of PPE-NMe3-Th, PPE-NMe3-DABCO, PPE-NMe3-OR8 and PPE-NMe3-SO3.
Figure 30:
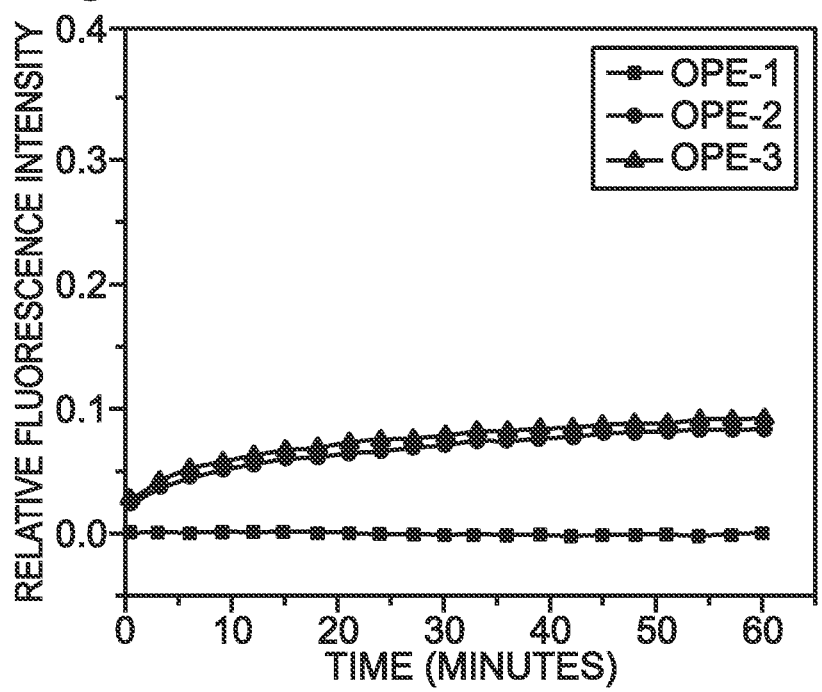
FIG. 30 is a graph of fluorescein leakage profiles from DOPG/DOPE (20/80) mixed vesicles with the addition of OPE-1, OPE-2 and OPE-3.
Figure 31:
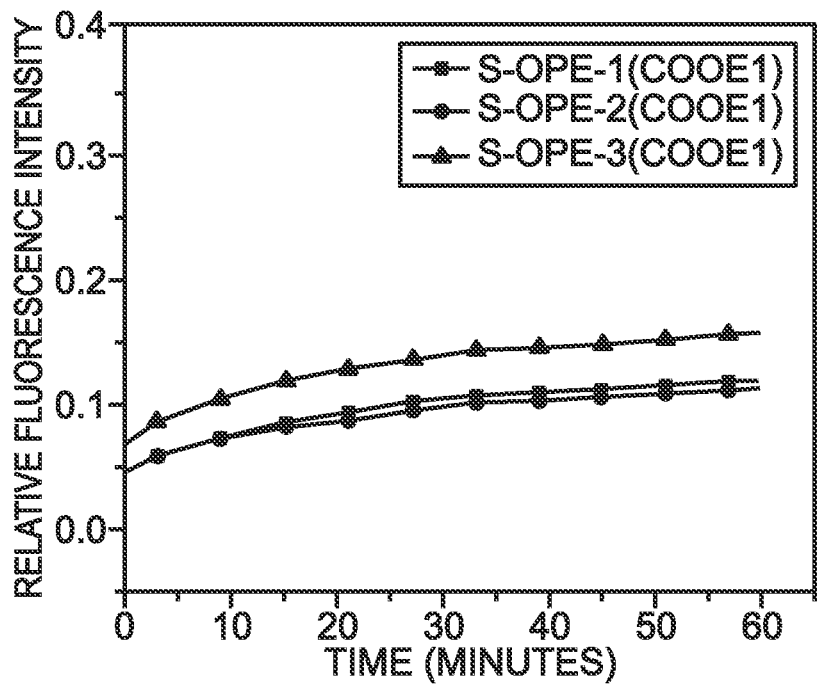
FIG. 31 is a graph of fluorescein leakage profiles from DOPG/DOPE (20/80) mixed vesicles with the addition of S-OPE-1(COOEt), S-OPE-2(COOEt), and S-OPE-3 (COOEt).
Figure 32:
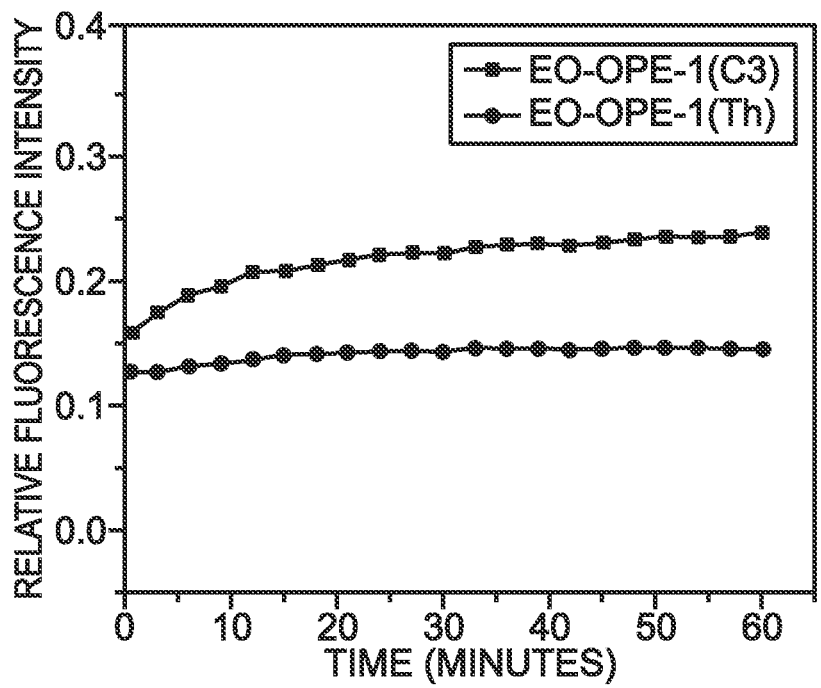
FIG. 32 is a graph of fluorescein leakage profiles from DOPG/DOPE (20/80) mixed vesicles with the addition of EO-OPE-1(C3) and EO-OPE-1(Th).
Figure 33:
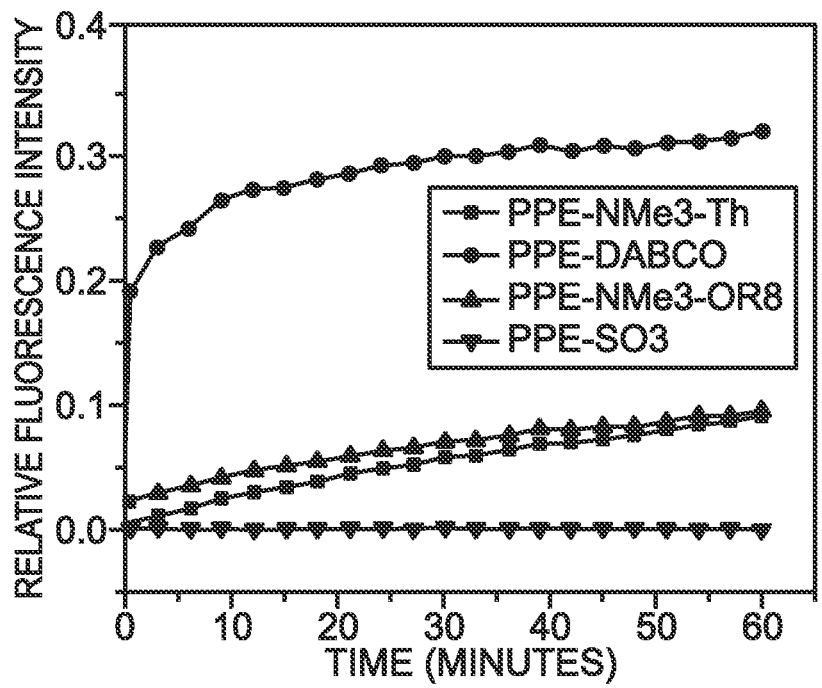
FIG. 33 is a graph of fluorescein leakage profiles from *E. coli* total lipid vesicles with the addition of PPE-NMe3-Th, PPE-NMe3-DABCO, PPE-NMe3-OR8 and PPE-NMe3-SO3.
Figure 34:
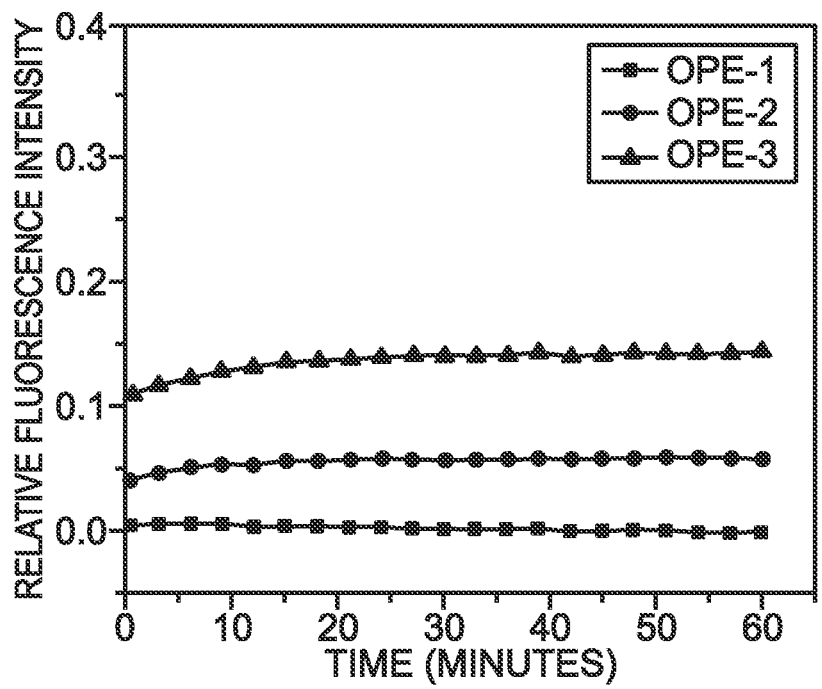
FIG. 34 is a graph of fluorescein leakage profiles from *E. coli* total lipid vesicles with the addition of OPE-1, OPE-2 and OPE-3.
Figure 35:
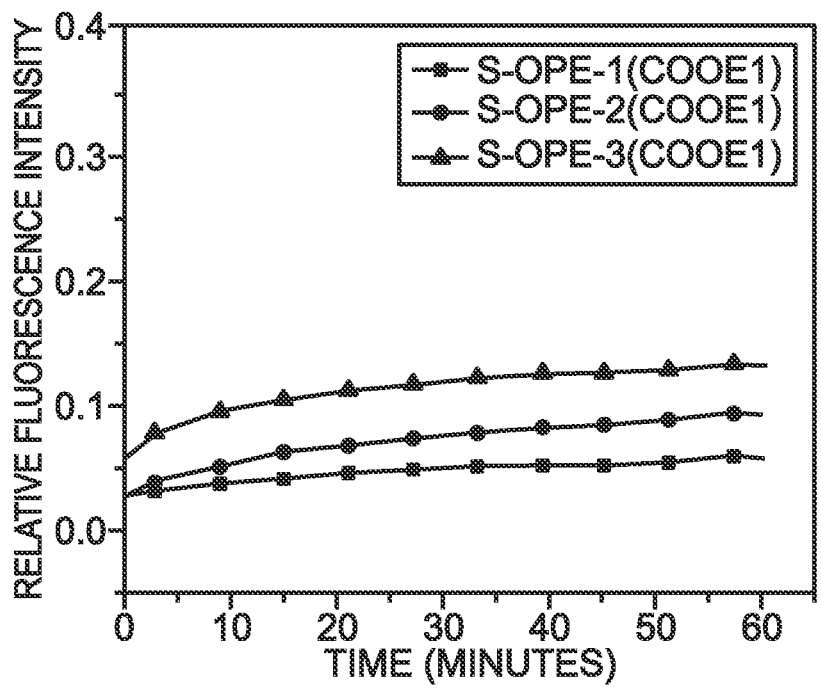
FIG. 35 is a graph of fluorescein leakage profiles from *E. coli* total lipid vesicles with the addition of S-OPE-1 (COOEt), S-OPE-2(COOEt), and S-OPE-3(COOEt).
Figure 36:
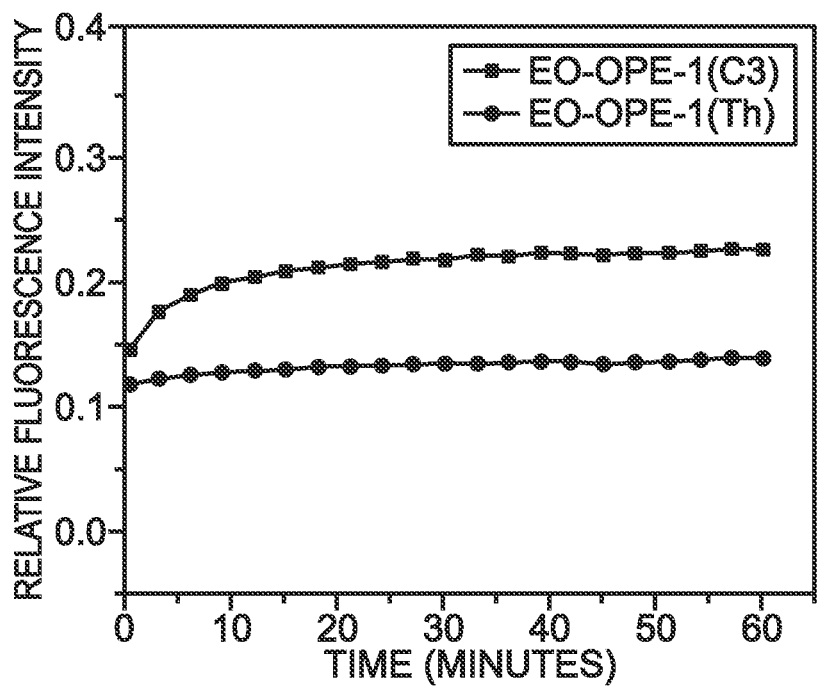
FIG. 36 is a graph of fluorescein leakage profiles from *E. coli* total lipid vesicles with the addition of EO-OPE-1(C3) and EO-OPE-1(Th).

FIGS. 22 and 23 show plots of biocidal activity based on chain length at concentrations of 1 and 10 ug/mL, respectively. At a high concentration (10 μg) of the polymer solutions (n=7 and 20) an Inner filter effect (little killing of bacteria) was seen. However, at low concentrations (1 μg) of the polymer solutions the shortest chain length of polymer shows the most effective light-induced biocidal activity. FIG. 24 shows flow cytometry results. Confocal Microscopy comparing control *E. Coli* and *E. Coli* after exposure to 1 ug/mL PPE-NMe3~7-COOEt and 120 min UV light irradiation show significant killing of bacteria.

Accordingly, it can be seen that the series of cationic CPEs shown and described herein exhibit chain length dependent photophysical properties and complexation with oppositely charged molecules. Furthermore, the shorter chain length of polymer shows more effective light-induced biocidal activity.

EXAMPLE II—Membrane Perturbation by PPE-NMe3-TH, PPE-DABCO, PPE-NMe3-OR8, PPE-SO3

Materials. The antimicrobial molecules were synthesized as described above. 1,2-dioleoyl-sn-glycero-3-phospho-(1'-rac-glycerol) (sodium salt) (DOPG), 1,2-dioleoyl-sn-glycero-3-phosphocholine (DO PC), 1,2-dioleoyl-sn-glycero-3-phosphoethanolamine (DOPE), *E. coli* total lipid, and cholesterol were purchased from Avanti Polar Lipids and used as received. 5(6)-carboxyfluorescein (hereafter referred to as fluorescein) was purchased from Sigma-Aldrich. Superfine Sephadex G-25 was obtained from GE Healthcare Bio-Science. All other chemicals were purchased from Sigma-Aldrich or Alfa Aesar. Ultrapure water was used throughout the study (Milli-Q, 18.2 MQ cm-1 resistivity)
Preparation of Fluorescein-Loaded Vesicles and Vesicle Leakage Assays.

Fluorescein-loaded large unilamellar vesicles (LUV) were prepared by extrusion. See e.g., Ding, L. P.; Chi, E. Y.; Chem_buru, S.; Schanze, K. S.; Lopez, G. P.; Whitten. D. G., Langmuir 2009, 25, 13742-13751. Briefly, a phospholipid stock solution was dried under a flow of nitrogen and then placed under vacuum overnight. The dried lipid film was then hydrated to 2-4 mM with 100 mM fluorescein in water (adjusted to pH 7 with NaOH) with strong shaking for 1 hr at a temperature above the phase transition temperature of the lipid. The resulting suspension was subjected to 4 freeze-thaw cycles. Finally, LUVs were formed by extruding the lipid solution 19 times through a 100 nm pore size polycarbonate membrane using a mini-extruder (Avanti Polar Lipids). Free fluorescein was removed from the dye-loaded vesicles by column filtration (Sephadex G-25 superfine). The mobile phase used was 200 mM NaCl containing 10 mM HEPES at pH 7. After separation, the phospholipid concentration of the dye-loaded vesicles was determined by the modified microprocedure of Barlett. (See, e.g., Bartlett, G. R., J. Bioi. Chem. 1959, 234, 466-468.) The hydrodynamic radii (Rh) of vesicles were determined by dynamic light scattering (DLS, DAWN HELEOS II, Wyatt Technology Corporation).

Vesicle membrane stability in the presence of PPE/OPE was evaluated by a dye-leakage assay. PPE or OPE was added to the dye-loaded vesicles at a (PPE/OPE):lipid molar ratio of 1:50 with a final lipid concentration between 0.2-0.3 mM. The concentration of polymer is based on polymer repeat unit. As the vesicle membrane is perturbed by the PPE or OPE, dye is released and the fluorescence intensity of released dye was recorded at 520 nm (excitation at 485 nm) (SpectroMax M-5 microplate reader, Molecular Devices). The CPE/OPE are not excited at this wavelength. Fluorescein leakage was calculated using equation (1):

$$\text{Fluorescein Leakage} = \frac{F - Fo}{F\max = Fo}$$

where F0 is the fluorescence intensity of the vesicles before the addition of PPE/OPE, F is the fluorescence intensity of the sample after the addition of PPE/OPE, and Fmax is the maximum fluorescence intensity of the sample, achieved by the addition of 1 μL 0.5 M Triton-XI 00 solution to 100 fJL of vesicles that caused complete lysis of the vesicles. Fluorescein leakage is taken as a measure of the extent of vesicle membrane disruption.
Results and Discussion It is widely accepted that the naturally occurring antimicrobial peptides and their synthetic mimics mainly target the lipid bilayer of the cell membrane. The phospholipid compositions of bacterial cell walls and mammalian cell membranes are very different. The principle phospholipid components in mammalian cell membranes are phosphatidylcholine (PC), phosphatidylethanolamine (PE), cholesterol, and sphingomyelin. Human erythrocyte cells contain mostly PC and 5-10% of negatively charged phosphatidylserine (PS) lipids. Because of the asymmetric distribution of erythrocyte membrane lipids, more than 95% of PS lipids reside on the inner leaflet of the membrane. Thus, the outer leaflet of the mammalian membrane is near neutral.9 On the other hand, the dominant lipids in the bacterial cytoplasmic membrane are phosphatidylglycerol (PG), PE, and diphosphatidylglycerol. Most Gram-negative bacterial membranes, including *E. coli*, contain 60-70% PE and 20-30% PG. As a result, the bacterial membrane is highly negatively charged. Based on the differences in lipid composition between mammalian and bacterial membranes, three vesicle compositions were studied. The membrane perturbation activities of the PPE/OPE used in this report were evaluated by fluorescein release assays (FIGS. 25-28).

Interaction with mammalian membrane mimic. V-1, composed of PC lipids and cholesterol, is used as a model for mammalian cell membranes. Only PPE-DABCO, EO-OPE-1(C3) and EO-OPE-1(Th) caused measurable membrane disruption against V-1 (FIGS. 25-28). All other PPE and OPE are inactive. (Note: "inactive" and "no release" refer to no dye release in excess to that of vesicles incubated alone through the entire incubation period).

Interaction with bacteria membrane mimics. V-2, composed of DOPG and DOPE, is used as a model for bacterial membranes. Most of the cationic PPE/OPE show good activity against V-2 (FIGS. 29-32). Specifically, PPE-NMe3-0R8, PPE-DABCO and EO-OPE-1(C3) induce approximately 20% dye release, PPE-NMe3-Th, OPE-2 and 3 and the three S-O PE-n oligomers cause ~1 0% release. In contrast, the anionic PPE-SO- and OPE-1, the shortest molecule tested (based on the distance along the long molecular axis), are inactive. V-3, made from *E. coli* total lipid extract, was used as a better mimic of the bacterial membrane. Dye leakage of the V-3 vesicles induced by PPE/OPE are comparable to the leakage induced in V-2 vesicles. (See FIGS. 33-36.) PPE-DABCO and OPE-3 were slightly more effective in inducing leakage in V-3 vesicles compared to V-2, and EO-OPE-1 (C3) and EO-OPE-1 (Th) caused a similar amount of dye leakage in V-2 and V-3. However, S-OPE-n caused a somewhat lower dye leakage in V-3 vesicles compared to V-2. Notably, OPE-1 and PPE-SO/- are still inactive against V-3 vesicles. It is worth noting that the active PPE/OPE exhibit concentration-dependent membrane disruption against V-3; at higher PPE/OPE:lipid ratios, higher levels of dye release were observed.

Conclusion

Results from our dye release experiments show that most PPE and OPE compounds used in this study selectively interact with specific types of membrane lipids. For the polymer series, the functional groups on the side chains dominate their membrane perturbation activity. Specifically, the high charge density and hydrophobic alkyl chains of PPE-DABCO's side chains give rise to the polymer's high perturbation activity against all the vesicles used. Not surprisingly, PPE-DABCO also has poor membrane selectivity. For the three oligomers studied, molecular length greatly influences their interactions with lipid bilayers. OPE-n and S-OPE-n exhibit size-dependent activity against bacterial membrane mimics, where longer oligomers exhibit higher activity than their smaller counterparts. EO-OPE, the oligomers without side chains, exhibit high membrane perturbation activity and poor selectivity. These results give us insights into the relationship between molecular structure and membrane perturbation ability of biocidal PPE and OPE. The observation that specific oligomers and polymers have high selectivity towards model bacterial membranes and little activity towards model mammalian membranes indicates these compounds may be efficient and yet non-toxic antimicrobials.

Example III—Antiviral Activity

We investigated the antiviral activity of PPEs and OPEs against MS2 and T4 bacteriophages. Bacteriophage MS2 is a non-enveloped ~27 nm RNA virus with a small genome of ~3600 single strand nucleotides, its morphology is very similar to picornaviruses, such as poliovirus and hepatovirus. Bacteriophage T4 is a relative large non-enveloped DNA virus with a 120 nm long by 86 nm wide head and approximately 100 nm long tail, it has a large genome of ~170 kbp double strand nucleotides. These bacteriophages are commonly employed for studies of environmental pollution and virus detection.

The isoelectric points of MS2 and T4 phage particles are 3.9 and 4-5 respectively, which endow them a slightly negative surface charge in a neutral buffer system, leading to ready association between phage particles and the cationic PPEs/OPEs. Previously we proposed that after exposure to UV-visible light the PPEs/OPEs can generate singlet oxygen followed by the generation of more corrosive reactive oxygen intermediates, because the conjugated pi bonding system within the backbone of PPEs/OPEs allows efficient intersystem crossing energy transfer. $^1O_2$ is known to significantly damage protein, which can account for their high light-activated antiviral ability.

In the current study, investigation of the light-activated and dark antiviral activity of PPEs/OPEs against two model viruses was reported. The destruction effect of PPEs/OPEs on the morphology of bacteriophage was explored by transmission electron microscope (TEM). Sodium dodecyl sulfate-polyacrylamide gel electrophoresis (SDS-PAGE) provided more insights into the light-activated inactivation mechanism.

Experimental Methods

Materials. The antimicrobial molecules were synthesized as described above. Luria broth and Agar were purchased from BD Biosciences. All other chemicals were purchased from Sigma-Aldrich or Alfa Aesar. The model bacteriophages—MS2 and T4 were purchased from the American Type Culture Collection (ATCC) along with their host bacteria, *E. coli* 15577 and *E. coli* 11303. Ultrapure water was used throughout the study (Milli-Q, 18.2 MΩ cm$^{-1}$ resistivity).

Bacteriophage Preparation and Titer. *E. coli* cells were grown in the standard Luria broth. The fresh *E. coli* culture was inoculated from an overnight culture followed by approximately three hours incubation at 37° C. to the exponential growth phase (O.D.$_{600}$~0.5). At this growth phase, the *E. coli* cells were collected by centrifuge and washed with *Escherichia coli* minimal medium (Glucose 5 g/L, Na$_2$HPO$_4$ 6 g/L, KH$_2$P$_4$ 3 g/L, NH$_4$Cl 1 g/L, NaCl 0.5 g/L, MgSO$_4$, 0.12 g/L, CaCl$_2$ 0.01 g/L, pH 7.2) twice. The cell pellet was resuspended with minimal medium. The phage stock solutions were added into their corresponding bacterial host suspensions the phage-bacteria mixture incubated for 15 minutes at 37° C. for infection. The phage-bacteria mixture was transferred into fresh *Escherichia coli* minimal medium and incubated overnight for viral replication. The phage solution was then centrifuged at 3500 rpm for 10 min, followed by filtering the supernatant with 0.22-µm cellulose ester membrane to remove remaining bacteria and bacterial debris. The phage titer was determined by plaque forming units (PFU). For PFU measurement, the exponential growth phase *E. coli* (ATCC 15597 and 11303 for MS2 and T4 bacteriophage, respectively) cells were incubated with the various dilution tubes of the phage solutions for 15 minutes at 37° C. then added into molten soft LB agar with gentle mixing. The soft agar mixture was then pouted onto pre-solidified LB plates. After 6-8 hours incubation, the plaque forming units were counted and phage solutions were diluted to $10^6$~$10^7$ PFU/ml with the minimal medium for further use.

Phage Inactivation. 10 ug/ml PPEs and OPEs were incubated with model virus solution in the dark or under UV-light for 1 hour. The UV-light irradiation experiments were carried out in a photoreactor (LZC-ORG, Luzchem Research Inc.). Two illumination sources were employed according to the different photophysical properties of PPEs/OPEs. UVA (centered at ~350 nm) and LZC-420 (centered at ~420 nm) were used to irradiate OPEs and PPEs respectively. The viral inactivation ability was determined by phage titer as stated above and calculated by log (N$_0$/N), where N is the PFU of the phage solution after exposure to PPEs/OPEs; N$_0$ represents the PFU of corresponding negative control (without PPEs, OPEs or UV-irradiation). The reported values were the average of duplicated measurements.

Transmission Electron Microscopy. High concentration of model viruses (~$10^{11}$ PFU/ml for T4 phage, ~$10^{12}$ PFU/ml for MS2 phage) and PPE/OPE (50 ug/ml) was used for TEM imaging (TEM images were generated in the UNM Electron Microscopy Shared Facility using a Hitachi H750 transmission electron microscope.) Phage samples were prepared by adding 5 uL phage solutions onto carbon-coated copper grids (freshly cleaned by plasma cleaner) and standing for 2 minutes then rinsing with pure water. The negative stain, 2% aqueous solution of uranyl acetate, was adding onto the grids and standing for 2 minutes, the excess stain was removed by filter paper. The grid was dried in air.

SDS-PAGE. The standard Laemmli protein gel electrophoresis method was used to examine the damage of phage capsid proteins. Electrophoresis was performed at 200V for 30 minutes after which the gels were stained with Coomassie brilliant blue R250 solution for 1 h.

Results and Discussion.

The phage titer assay described herein was done by a series dilution of the phage-PPEs/OPEs mixture and incubating each diluted sample with the corresponding E. coli host cells within molten soft LB agar. Since our previous work demonstrated that the PPEs/OPEs can strongly inactive E. coli cells, which may interface the plaque assay, it is necessary to study the effect of these residual PPEs/OPEs on the E. coli host cells. For the control experiment without phage and PPEs/OPEs, the E. coli cells can form a uniform bacterial lawn on the surface of soft agar after 6 hours incubation at 37° C. Under current experimental condition, 0.33 ug/ml was the maximum concentration of PPEs/OPEs within the soft agar, which can not cause any obvious defect on the bacterial lawn at the same condition.

Figure 37:
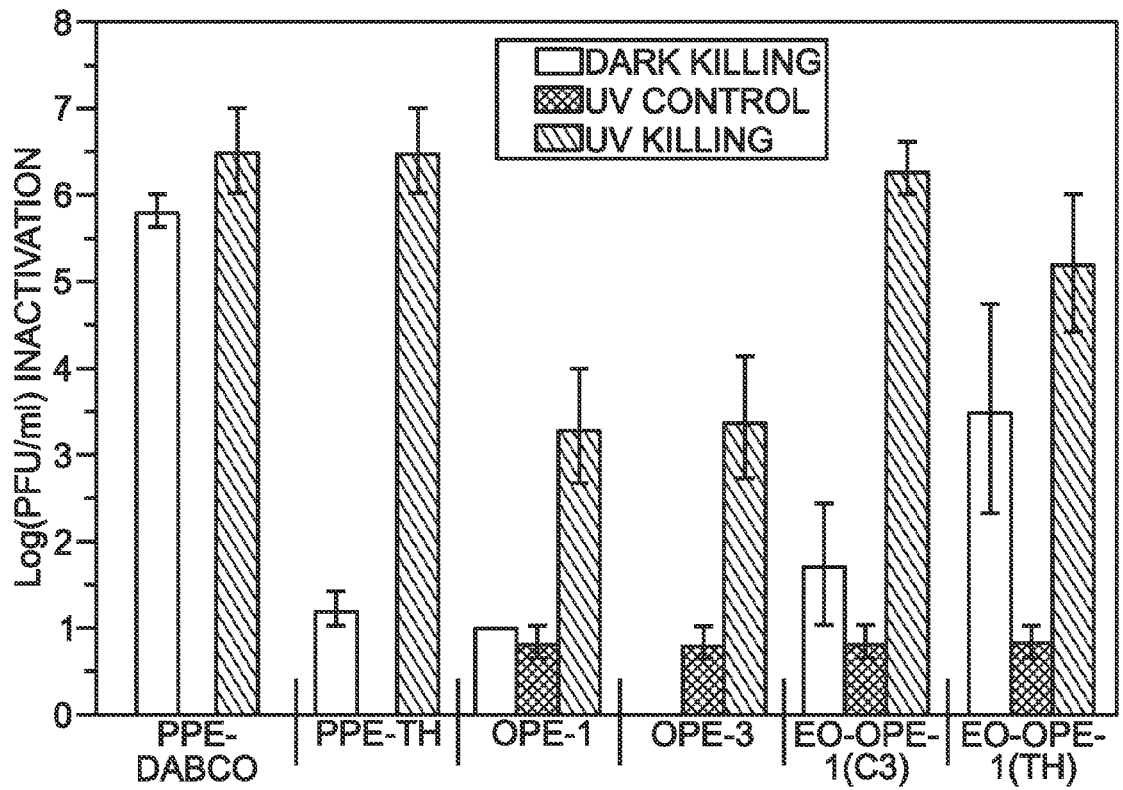
FIG. 37 shows inactivation of bacteriophage MS2 by PPEs in the dark and under UV-light irradiation for 1 hour.
Figure 38:
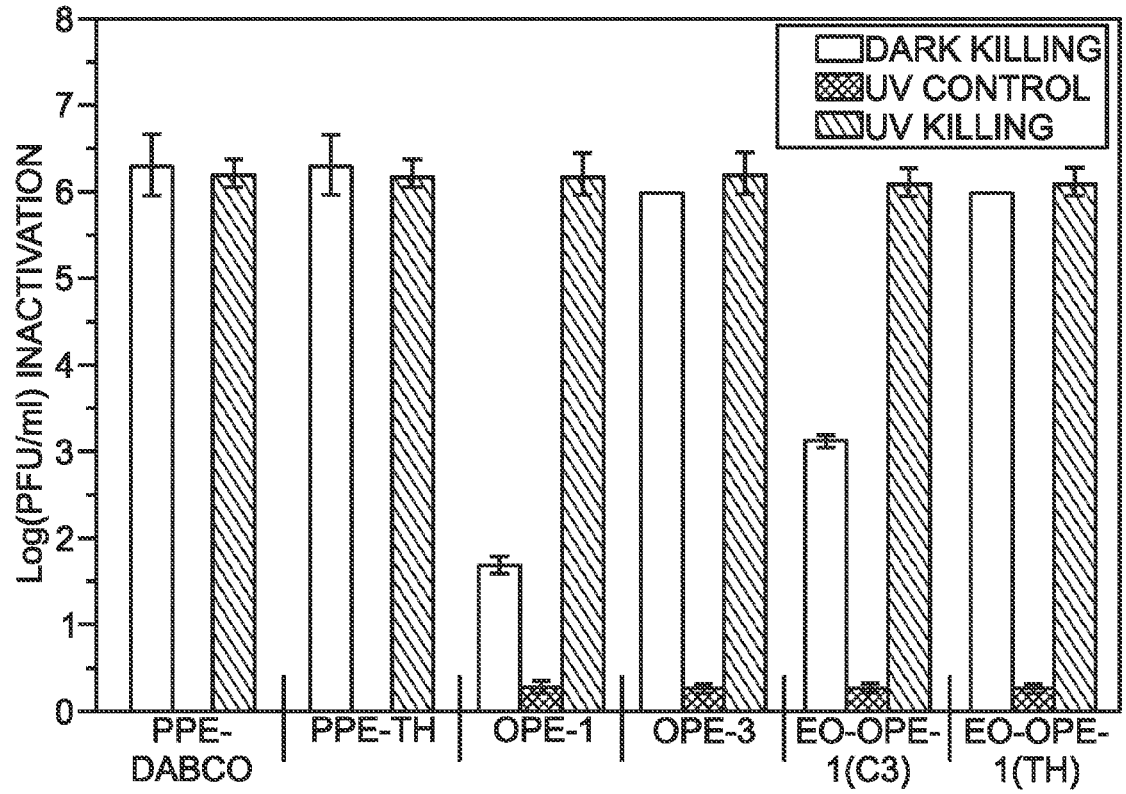
FIG. 38 shows inactivation of bacteriophage T4 by OPEs in the dark and under UV-light irradiation for 1 hour.

Phage Inactivation. FIGS. 37 and 38 depict the phage inactivation under different conditions: PPEs/OPEs in the dark, UV irradiation alone and UV sensitized PPEs/OPEs. PPE-DABCO and EO-OPE-1(Th) exhibit significant dark antiviral activity against T4 phage. PPE-Th, OPE-1 and EO-OPE-1(C3) can inactivate more than 90% T4 phage in the dark. However, no dark inactivation ability was observed for OPE-3 against T4 phage. Enhanced inactivation of T4 phage was observed by PPEs/OPEs in the presence of UV irradiation. Compared with T4 Phage, all of the PPEs/OPEs produce more efficient dark inactivation of MS2; except OPE-1 and EO-OPE-1(C3), all other compounds show more than 6-log inactivation ability against MS2. Meanwhile, enhanced inactivation of MS2 phage was observed by OPE-1 and EO-OPE-1(C3) in the presence of UV irradiation. It is worthwhile to note that the long wavelength UV-visible light (LZC-420) produce negligible inactivation of the model viruses. In contrast, UVA irradiation causes obvious inactivation of T4 phage and moderate inactivation of MS2 phage. The different effects of UVA light on the model viruses can be partially attributed to the following reasons: upon exposure to UVA irradiation, adjacent thymidine residues within T4 phage genome are covalently linked to form thymidine dimmers,[8] leading to the inactivation of T4 phage. In addition, the genome of T4 phage is almost 47 times larger than that of MS2 phage, as a result, T4 phage is more vulnerable to UVA. The T4 bacteriophage infection mechanism has been extensively studied and well established, it recognizes lipopolysaccharide and the OmpC protein on the surface of E. coli cell followed by the injection of phage genome into the host cell and replication of phage particle.[9] However, the infection mechanism of MS2 phage is not quite clear, it is believed that the pilus of E. coli cell are the receptors for MS2 phage.[10] It is reasonable to propose that the PPEs and OPEs can associate with the model viruses through electrostatic interaction followed by the damage of viral capsid and/or the inhabitation the binding of viral particle towards host E. coli cell, upon the direct contact between these compounds and model viruses. According to our previous work,[3a] the enhanced antiviral activity of these compounds in the presence of UV-light can be proposed to the generation of corrosive reactive oxygen species after exposure to UV-visible light, which can strongly damage biomolecules.[7, 11] Subsequent results confirm the damage of viral capsid caused by PPE-DABCO and EO-OPE-1(Th).

Figure 39:
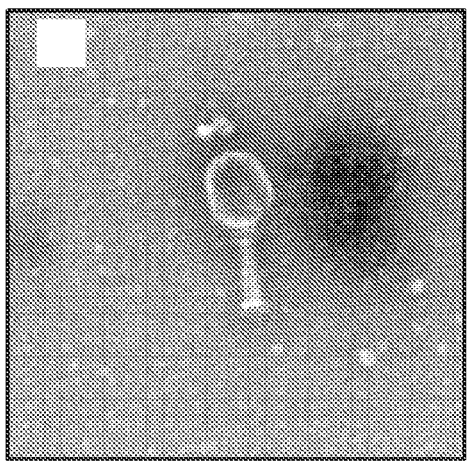
FIG. 39 is a TEM image of uranyl acetate negatively stained model T4 virus alone.
Figure 40:
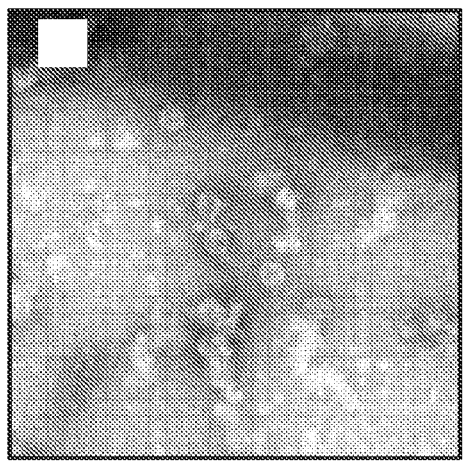
FIG. 40 is a TEM image of uranyl acetate negatively stained model MS2 virus alone.
Figure 41:
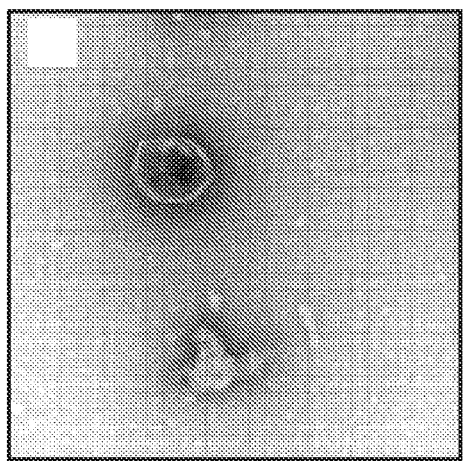
FIG. 41 is a TEM image of uranyl acetate negatively stained T4 phage with PPE-DABCO, dark.
Figure 42:
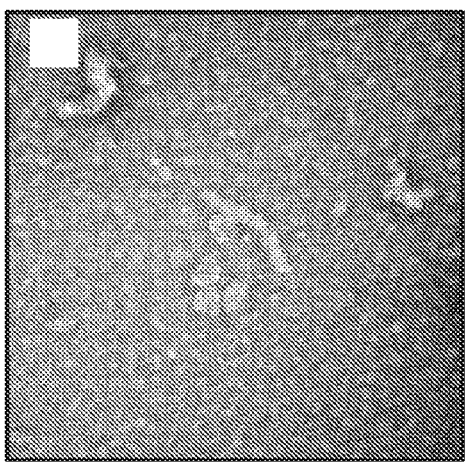
FIG. 42 is a TEM image of uranyl acetate negatively stained MS2 phage with PPE-DABCO, dark.
Figure 43:
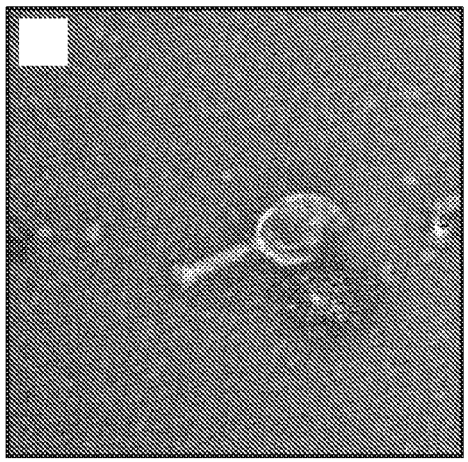
FIG. 43 is a TEM image of uranyl acetate negatively stained T4 phage with PPE-DABCO, LZC-420.
Figure 44:
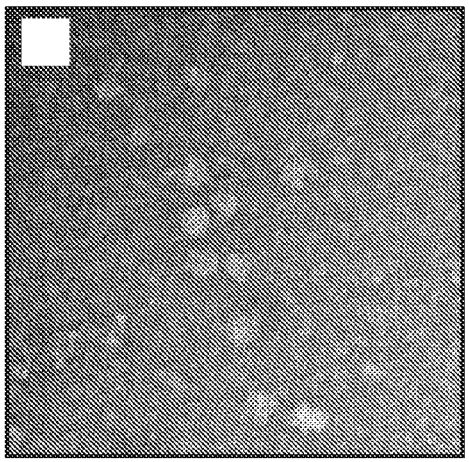
FIG. 44 is a TEM image of uranyl acetate negatively stained MS2 phage with PPE-DABCO, LZC-420.
Figure 45:
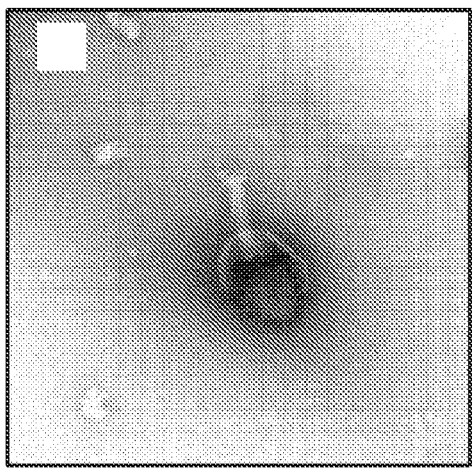
FIG. 45 is a TEM image of uranyl acetate negatively stained T4 phage with EO-OPE(Th), dark.
Figure 46:
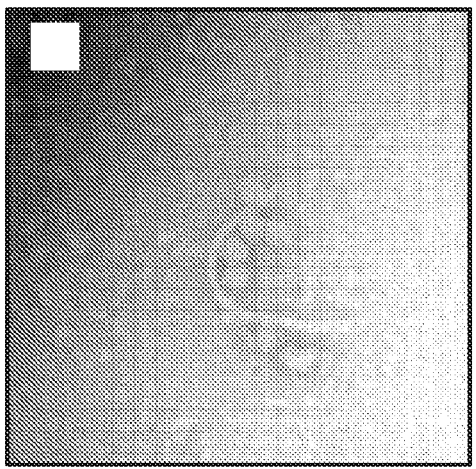
FIG. 46 is a TEM image of uranyl acetate negatively stained MS2 phage with EO-OPE(Th), dark.
Figure 47:
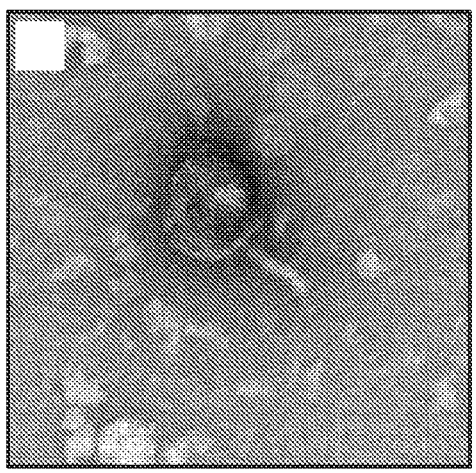
FIG. 47 is a TEM image of uranyl acetate negatively stained T4 phage with EO-OPE(Th), UVA.
Figure 48:
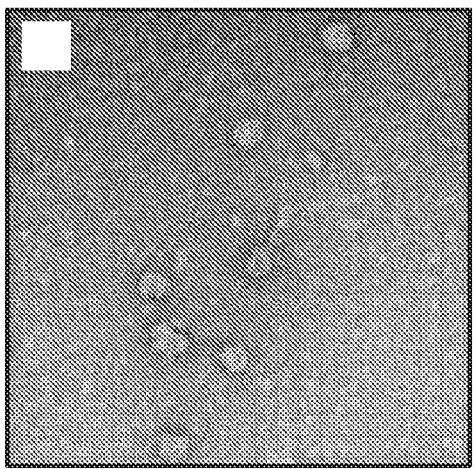
FIG. 48 is a TEM image of uranyl acetate negatively stained MS2 phage with EO-OPE(Th), UVA.

Viral Morphology Damage. To visualize the viral morphology damage by PPE-DABCO and EO-OPE-1(Th), samples immobilized on carbon-coated grids were imaged by TEM, as shown in FIGS. 38-47. More than 10 images were taken for each sample to guarantee the reproducibility of the observed viral damage. The untreated T4 phage maintains its classic morphology with intact head and tail structure (FIG. 39). In contrast, serious damage happens to the PPE-DABCO and EO-OPE-1(Th) treated T4 phage (FIGS. 41, 43, 45, and 47). Likewise, the shape of the intact MS2 phage is uniform and the size is very close to the literature report value (FIG. 40). Obvious morphology change observed for the PPE-DABCO and EO-OPE-1(Th) treated MS2 phage, which are withered and formless (FIGS. 42, 44, 46 and 48). Even though not conclusive, ample amounts of doubtful PPE-DABCO and EO-OPE-1(Th) aggregates are visible close to MS2 and T4 phages (data not shown), which imply the efficient association between PPEs/OPEs and model viruses.

Example IV—Antimicrobial Activity

The activity of PPE-DABCO against S. cerevisiae was examined. S. cerevisiae was cultered, counted by a coulter counter and diluted $10^7$ mL$^{-1}$ in PBS. The suspended culture was then exposed to 0.13 mM in PPE-DABCO for 30 minutes while irradiating with Fiber-Lite 190 and then stained with SYTO 9 and PI (Fungalight™) for 30 minutes. Flow cytometry was then used to count percentage of dead yeast. A control sample (S. cerevisiae without exposure to PPE-DABCO) showed 10% dead while the treated samples showed 29-30% dead.

Example V—Photo-chemical Self-protecting

A study of the photochemical reaction processes of a model cationic oligomer based on the p-Phenylene-Ethynylene repeat unit is performed in aqueous solution both in the presence and absence of oxygen. Clearly different reaction pathways were observed with this model compound in the presence and absence of oxygen in aqueous solution. The products of these reactions were followed spectroscopically by UV-Vis Spectroscopy and characterized by Mass Spectrometry. The results of this study revealed the photoaddition of water across the triple bond of the ethynyl group in absence of oxygen, and a possible cycloaddition of oxygen across the triple-bond in the presence of oxygen. A study of PPE-SO3 indicates that when this material is photolyzed in water in the presence of air, the addition of oxygen can lead to a protection of the polymer from extensive photobleaching may occur via the oxygen adduct acting as a trap site still capable of reactive oxygen species generation.

Figure 49:
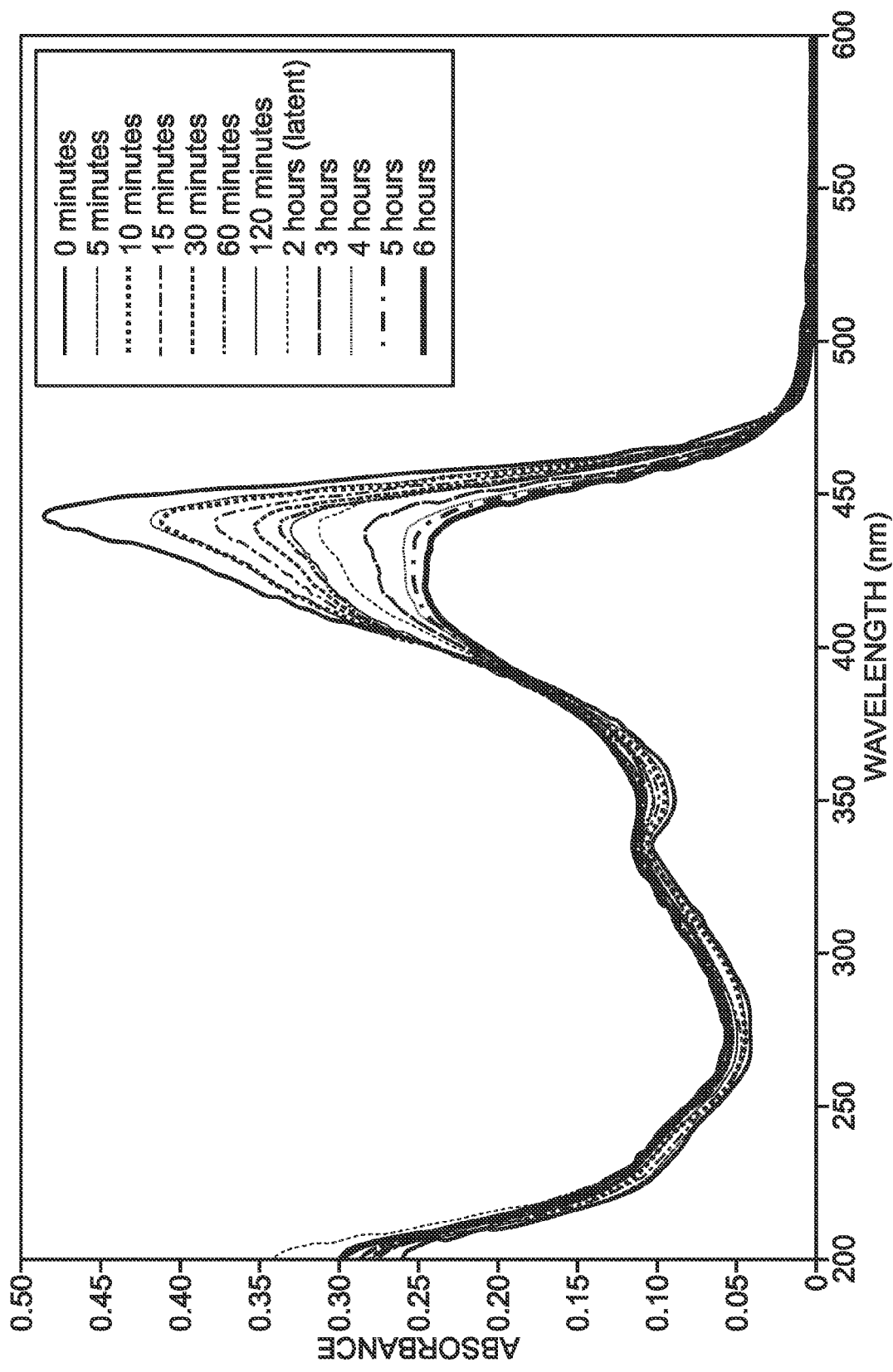
FIG. 49 shows the photolysis of PPE-SO3 in water.

As can be seen from the structure shown in FIG. 3, PPE-SO3 has anionic side groups on each repeat unit. A photobleaching reaction was followed spectroscopically as shown in FIG. 49. There are several aspects of the limited photodegradation that are important to note. The photobleaching of the PPE-SO3 is very clean. However the photobleaching is much slower than smaller polymers and appears to terminate before a major fraction of the long wavelength transition has disappeared. That there is no major shift in the absorption spectrum is consistent with our previous finding that p-phenylethynylene polymers likely exist as a chain with a series of "segment chromophores" that serve to break the polymer into several isolated conjugated segments with a break in the conjugation between the "segment chromophores". For the photoreactions reported in this study there is a small, but likely significant, grow-in at wavelengths extending beyond the starting material. For the aerated solutions this is consistent with the presence of a long wavelength absorbing 1,2-diketone that could readily be generated following cycloaddition of dioxygen to a triple bond and subsequent cleavage of the cycloadduct. A 1,2-diketone "trap" absorbing in the visible region (biacetyl is yellow but weakly absorbing) could act as a trap and intercept either singlet or triplet excitation hopping between segment chromophores. The biacetyl triplet (ET=57 kcal/mole)22 is sufficiently energetic to generate singlet oxygen but once biacetyl triplets are generating singlet oxygen it becomes more and more probable that the singlet oxygen is generated remote from a segment chromophore and less likely to cause a degradative reaction. Thus the photochemical generation of a trap that drains excitation energy from the segment chromophore can provide a protection of remaining segment chromophores of the polymer and attenuate photobleaching. Since the trap can generate singlet oxygen the light activated antimicrobial activity may still be retained.

What is claimed is:

1. A material incorporating a poly(phenylene ethynylene), the poly(phenylene ethynylene) having the structure:

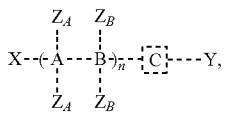

wherein
the poly(phenylene ethynylene) is grafted to the material by chemisorption or wherein the polymer is attached to the material by physisorption;
n is selected from the group consisting of whole numbers between 5 and 200;
A is $C_2C_6H_2$;
B is selected from the group consisting of $C_2C_6H_2$ and $C_2C_4S$;
C= is either $C_6H_4$ or not present;
X is selected from the group consisting of: $[C_2C_6H_4]_2COOCH_2CH_3$ and $[C_2C_4H_2S][C_2C_6H_4]COOCH_2CH_3$;
Y is selected from the group consisting of: $COOCH_2CH_3$;
$Z_A$ is selected from the group consisting of $O(CH_2)_k(C_6H_{12}N_2)C_6H_{13}^{2+}$, $O(CH_2)_kSO_3^-$, and $O(CH_2)_kN(CH_3)_3^+$; where k is selected from the group consisting of the whole number between 1 and 10;
$Z_B$ is H;
if $Z_A$ is $O(CH_2)_k(C_6H_{12}N_2)C_6H_{13}^{2+}$, then $A=C_2C_6H_2$, C is $C_6H_4$, Y is $COOCH_2CH_3$, and X is $[C_2C_6H_4]_2COOCH_2CH_3$; and
if $Z_A$ is $O(CH_2)_kN(CH_3)_3^+$ and C is present, then $Y=COOCH_2CH_3$ and X is selected from the group consisting of $[C_2C_6H_4]_2COOCH_2CH_3$ and $[C_2C_4H_2S][C_2C_6H_4]COOCH_2CH_3$, wherein
if $B=C_2C_6H_2$, then X is $[C_2C_6H_4]_2COOCH_2CH_3$, and
if $B=C_2C_4S$, then X is $[C_2C_4H_2S][C_2C_6H_4]COOCH_2CH_3$.

2. The material of claim 1 wherein A and $B=C_2C_6H_2$, $C=C_6H_4$, $X=[C_2C_6H_4]_2COOCH_2CH_3$, $Y=COOCH_2CH_3$, and $Z_A=O(CH_2)_kN(CH_3)_3^+$.

3. The material of claim 1 wherein A and $B=C_2C_6H_2$, $C=C_6H_4$, $X=[C_2C_6H_4]_2COOCH_2CH_3$, $Y=COOCH_2CH_3$, and $Z_A=O(CH_2)_k(C_6H_{12}N_2)C_6H_{13}^{2+}$.

4. The material of claim 1 wherein $A=C_2C_6H_2$, $B=C_2C_4S$, $C=C_6H_4$, $X=[C_2C_6H_4]_2COOCH_2CH_3$, $Y=COOCH_2CH_3$, and $Z_A=O(CH_2)_kN(CH_3)_3^+$.

5. The material of claim 1 wherein k=3.

6. The material of claim 1 wherein the material exhibits biocidal activity.

7. The material of claim 1 wherein the material exhibits antiviral activity.

8. The material of claim 1 wherein the material exhibits antifungal activity.

9. The material of claim 1, wherein the poly(phenylene ethynylene) is functionally attached to the material so that the poly(phenylene ethynylene) can interfere with the pathogenicity of a pathogen that contacts the poly(phenylene ethynylene).

10. The material of claim 1 wherein the material is a fiber, or a textile formed therefrom.

11. The material of claim 10 wherein the fiber or textile comprises a natural fiber, a synthetic fiber, or both.

12. The material of claim 11 wherein the natural fiber is cotton, silk, or wool, or a blend thereof.

13. The material of claim 11 wherein the synthetic fiber is rayon or nylon.

14. The material of claim 11 wherein the synthetic fiber is produced by electrospinning.

15. The material of claim 10 wherein the fiber or textile is comprised by an object that is potentially contaminated with a microorganism or a virus.

16. The material of claim 15 wherein the object is a wound treatment, a bandage, a swab, a sterile mat, a liner, or a filter for water purification.

17. The material of claim 15 wherein the object is a mattress, a bed linen, a countertop covering, a tablecloth, or a curtain.

* * * * *

UNITED STATES PATENT AND TRADEMARK OFFICE
CERTIFICATE OF CORRECTION

PATENT NO.        : 9,527,806 B2
APPLICATION NO.   : 13/809572
DATED             : December 27, 2016
INVENTOR(S)       : Whitten et al.

Page 1 of 1

It is certified that error appears in the above-identified patent and that said Letters Patent is hereby corrected as shown below:

On page 2, in Column 1, item (56) References Cited, under "Other Publications", Line 16, delete "Prelimary" and insert --Preliminary--, therefor On page 3, in Column 1, item (56) References Cited, under "Other Publications", Line 8, delete "Witten" and insert --Written--, therefor On page 3, in Column 2, item (56) References Cited, under "Other Publications", Line 9, delete "Opitical," and insert --Optical,--, therefor On page 3, in Column 2, item (56) References Cited, under "Other Publications", Line 50, delete "Ethynyiene" and insert --Ethynylene--, therefor Signed and Sealed this
Third Day of April, 2018

Andrei Iancu
*Director of the United States Patent and Trademark Office*